(12) United States Patent
Cargill et al.

(10) Patent No.: US 9,464,329 B2
(45) Date of Patent: Oct. 11, 2016

(54) PORTABLE SYSTEMS AND METHODS FOR AMPLIFYING NUCLEOTIDES AND DETECTING NUCLEOTIDE SEQUENCES

(75) Inventors: Edward J. Cargill, Chesterfield, MO (US); Kevin L. Deppermann, St. Charles, MO (US); Brad D. White, Creve Coeur, MO (US); William A. Grote, Fenton, MO (US); Elias J. Yannakakis, Chesterfield, MO (US); Andrew M. Singleton, Manchester, MO (US); G. David Grothaus, Emerald Isle, NC (US); Tiffany L. Stephans, Eureka, MO (US); Allen T. Christian, Wildwood, MO (US); Donald W. Mittanck, Ballwin, MO (US); Yelena A. Dudin, Town and Country, MO (US); Ramesh Govinthasamy, Maryland Heights, MO (US)

(73) Assignee: MONSANTO TECHNOLOGY LLC, St. Louis, MO (US)

(*) Notice: Subject to any disclaimer, the term of this patent is extended or adjusted under 35 U.S.C. 154(b) by 812 days.

(21) Appl. No.: 13/637,303

(22) PCT Filed: Mar. 17, 2011
(Under 37 CFR 1.47)

(86) PCT No.: PCT/US2011/028806
§ 371 (c)(1),
(2), (4) Date: Oct. 4, 2013

(87) PCT Pub. No.: WO2011/119404
PCT Pub. Date: Sep. 29, 2011

(65) Prior Publication Data
US 2015/0203922 A1 Jul. 23, 2015

Related U.S. Application Data

(60) Provisional application No. 61/317,911, filed on Mar. 26, 2010.

(51) Int. Cl.
*C12Q 1/68* (2006.01)
*G01N 21/64* (2006.01)

(52) U.S. Cl.
CPC ........... *C12Q 1/6895* (2013.01); *C12Q 1/6844* (2013.01); *G01N 21/643* (2013.01);
(Continued)

(58) Field of Classification Search
CPC .............. C12Q 1/6895; C12Q 1/6844; C12Q 2600/13; G01N 21/645; G01N 2201/0221; G01N 2201/061; G01N 2201/062; G01N 2201/6421
See application file for complete search history.

(56) References Cited

U.S. PATENT DOCUMENTS

| 6,586,754 B1 | 7/2003 | Hultermans |
| 6,646,264 B1 | 11/2003 | Modiano et al. |
| 2003/0127609 A1 | 7/2003 | El-Hage et al. |

(Continued)

OTHER PUBLICATIONS

PCT International Search Report and Written Opinion of the International Searching Authority mailed on May 20, 2011 regarding PCT/US2011/028806; pp. 9.

*Primary Examiner* — Brian R Gordon
(74) *Attorney, Agent, or Firm* — James E. Davis

(57) ABSTRACT

Portable systems and methods for amplifying nucleotides and for detecting nucleotide sequences in a sample are provided. The portable instruments and methods use RPA techniques for DNA amplification and detect sample fluorescence in response to amplification and/or to the presence of specific DNA sequences.

13 Claims, 26 Drawing Sheets

(52) U.S. Cl.
CPC ......... *G01N21/645* (2013.01); *C12Q 2600/13* (2013.01); *G01N 2021/6421* (2013.01); *G01N 2021/6432* (2013.01); *G01N 2021/6441* (2013.01); *G01N 2201/024* (2013.01); *G01N 2201/0221* (2013.01); *G01N 2201/062* (2013.01); *G01N 2201/0627* (2013.01)

(56) References Cited

U.S. PATENT DOCUMENTS

| | | |
|---|---|---|
| 2005/0068534 A1 | 3/2005 | Kleinfeld et al. |
| 2007/0141859 A1 | 6/2007 | Ishihara et al. |
| 2008/0241098 A1 | 10/2008 | Young et al. |
| 2009/0136963 A1 | 5/2009 | Breidenthal et al. |

PORTABLE SYSTEMS AND METHODS FOR AMPLIFYING NUCLEOTIDES AND DETECTING NUCLEOTIDE SEQUENCES

FIELD OF THE DISCLOSURE

The field of this disclosure relates to portable systems and methods for amplifying nucleotides and for detecting nucleotide sequences in a sample and, more particularly, portable instruments and methods that detect sample fluorescence in response to amplification and/or to the presence of a nucleotide sequence of interest.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Advances in crop science and biotechnology have led to specialty crops that have one or more desirable traits. Examples of such traits include, drought-resistance, pesticide tolerance (e.g., glyphosate tolerance), high-yielding crops, seeds with desirable fatty-acid profiles (e.g., as in low-linoleic acid soybeans), high-oil seeds, insect tolerance (e.g., corn-bore resistance) and the like. There is an increasing need to test commodity crops to determine whether they possess altered DNA sequences that express such traits. Biotech products may be analyzed by testing for proteins that are expressed by the modified DNA sequences. However, such techniques are not capable of distinguishing between plant varieties that produce the same recombinant proteins. In such instances, the plant is tested by analyzing whether the plant DNA contains the specific DNA sequence that results in expression of the trait.

Conventionally, these DNA sequences are detected by gathering a sample and transporting the sample to an off-site laboratory. The sample may be processed by extracting template DNA and amplifying the DNA by polymerase chain reaction ("PCR") techniques. PCR amplifies template DNA by use of two oligonucleotide primers, an agent for polymerization, a target nucleic acid template and successive cycles of denaturation of nucleic acid and annealing and extension of the primers to produce a large number of copies of a particular nucleic acid segment. With this method, segments of single copy genomic DNA can be amplified more than 10 million fold with very high specificity and fidelity. PCR typically requires thermocycling equipment and equipment to monitor reaction kinetics if detected in real-time. Typically, secondary equipment (e.g. fluorescence detector) and methods (e.g. gel electrophoresis) are used to detect amplified DNA after the conclusion of amplification. This equipment is bulky and requires technical skill to operate, which prevents the equipment from remote-use applications (e.g., point-of-grain delivery) by unskilled users.

As an alternative to PCR techniques, an analysis method known as recombinase polymerase amplification (RPA) has been developed. RPA techniques can amplify a single copy of DNA and can amplify DNA under generally isothermal conditions. Moreover, RPA analysis can be performed in about 15 minutes and does not require sample purification.

While RPA analysis may be preferred over PCR analysis, RPA conventionally is also performed in a laboratory by highly trained personnel. Typically the equipment used for analysis is capable of analyzing a number of samples (e.g., well plates) which results in the equipment being bulky and of limited portability. Further, the equipment is of high complexity (e.g., uses sophisticated mixing techniques and programmable software) which results in increased cost. A continuing need exists for portable and simplified instruments and methods for detecting nucleotide sequences (i.e., genes, markers, molecular events) in plants (e.g., soybeans) and equipment and, particularly, systems that use RPA amplification.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with the present disclosure, a portable system for detecting nucleotide sequences in a sample is described. In one or more embodiments, the system is capable of detecting two or more amplified DNA sequences. For instance, the system may contain multiple sets of optics that allow the system to detect a first DNA sequence that is associated with the plant in general to use as an internal control and a second DNA sequence associated with a modified trait (e.g., pesticide tolerance) of the plant. Generally, the instruments of the present disclosure use multiple fluorophores that fluoresce in the presence of the DNA sequences. Fluorescence may be measured to determine whether the DNA sequences were present in the sample. The instrument may use RPA amplification techniques and uses vibratory motors and solid couplings for simplified mixing operations.

In one aspect of the present disclosure, a portable system for detecting fluorescence emitted from a sample includes a first optics module, a second optics module and a sample module for holding a sample in the optical pathway of the first optics module and the second optics module. The first optics module, second optics module and sample module are attached to a mounting plate. The first optics module includes a first optics module housing, a first excitation filter, a first dichroic mirror, a first lens and a first emission filter. The second optics module includes a second optics module housing, a second excitation filter, a second dichroic mirror, a second lens and a second emission filter. The sample module includes a sample module housing, a vibratory motor, a solid coupling for receiving a sample vial, the solid coupling being attached to the vibratory motor and a vibratory insulating spacer attached to the vibratory motor to prevent vibrations from traveling to the mounting plate and to the first and second optics modules during operation of the vibratory motor. The first optics module housing and the second optics module housing are separated from the sample module housing.

Another aspect of the present disclosure is directed to a method for determining whether a first DNA sequence and a second DNA sequence are present in a sample by use of a portable system. The portable system includes a first optics module, a second optics module and a sample module. The first optics module, second optics module and sample module are attached to a mounting plate. The first optics module includes a first optics module housing, a first excitation filter, a first dichroic mirror, a first lens and a first emission filter. The second optics module includes a second optics module housing, a second excitation filter, a second dichroic mirror, a second lens and a second emission filter. The sample module includes a sample module housing, a heating element, a vibratory motor, a solid coupling for receiving the sample vial, the solid coupling being attached to the vibratory motor, and a vibratory insulating spacer attached to the vibratory motor to prevent vibrations from traveling to the mounting plate during operation of the vibratory motor. The first optics module housing and the second optics module housing are separated from the sample module housing. According to the method, template DNA and RPA reagents are combined in a reaction vial to form a reaction mixture. The reaction vial is placed in the sample module of the portable system. Power is applied to the vibratory motor to cause the solid coupling to vibrate. Vibration of the solid coupling translates to the reaction mixture to cause mixing of the reaction mixture. The reaction mixture is incubated by use of the heating element to an amplification temperature at which DNA is amplified by an RPA process to form an amplified sample mixture. Power is applied to a first light source to cause light to travel through the first optics module and to the amplified sample mixture to cause the sample mixture to fluoresce. Power is applied to a second light source to cause light to travel through the second optics module and to the amplified sample mixture to cause the sample mixture to fluoresce. The intensity of fluorescence of the amplified sample mixture after application of the first light source is correlated to the presence of the first DNA sequence in the DNA segment. The intensity of fluorescence of the amplified sample mixture after application of the second light source is correlated to the presence of the second DNA sequence in the DNA segment.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

Figure 1:
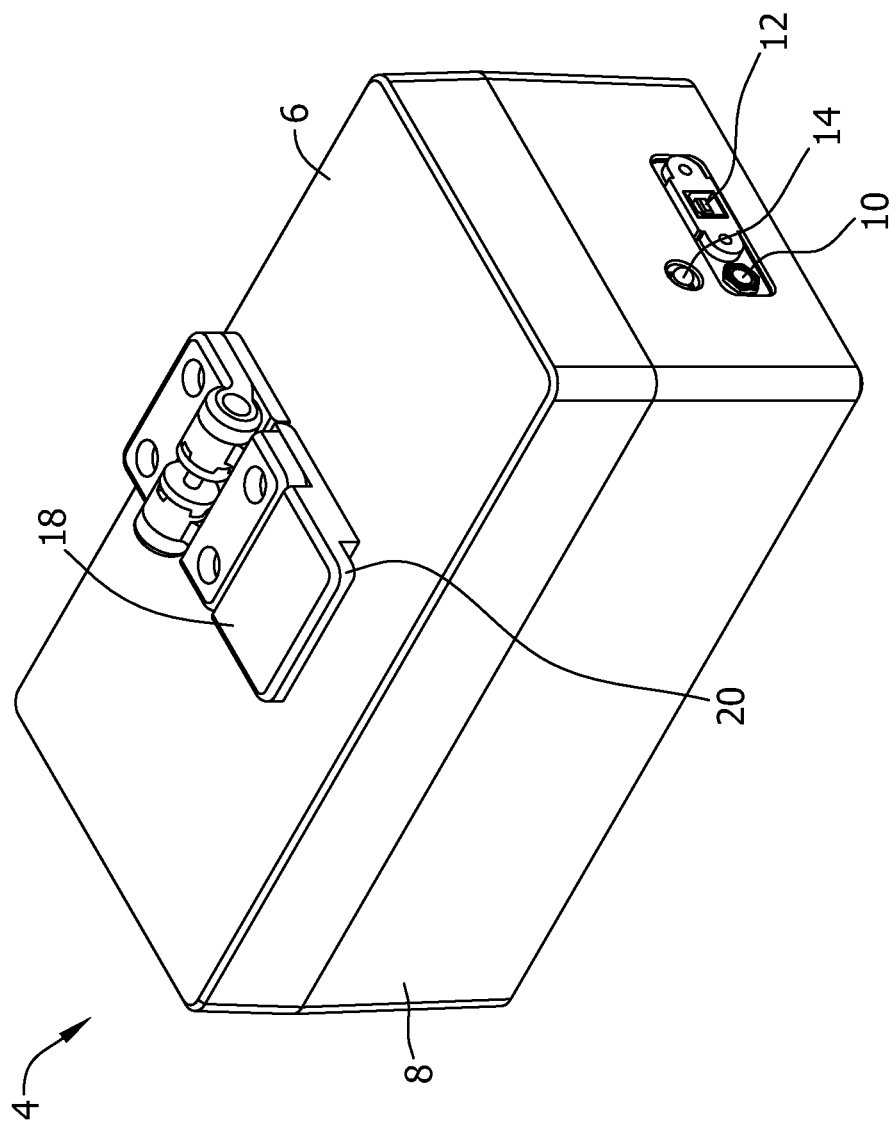
FIG. 1 is a perspective view of one embodiment of the portable system of the present disclosure showing the hinged cover closed.
Figure 2:
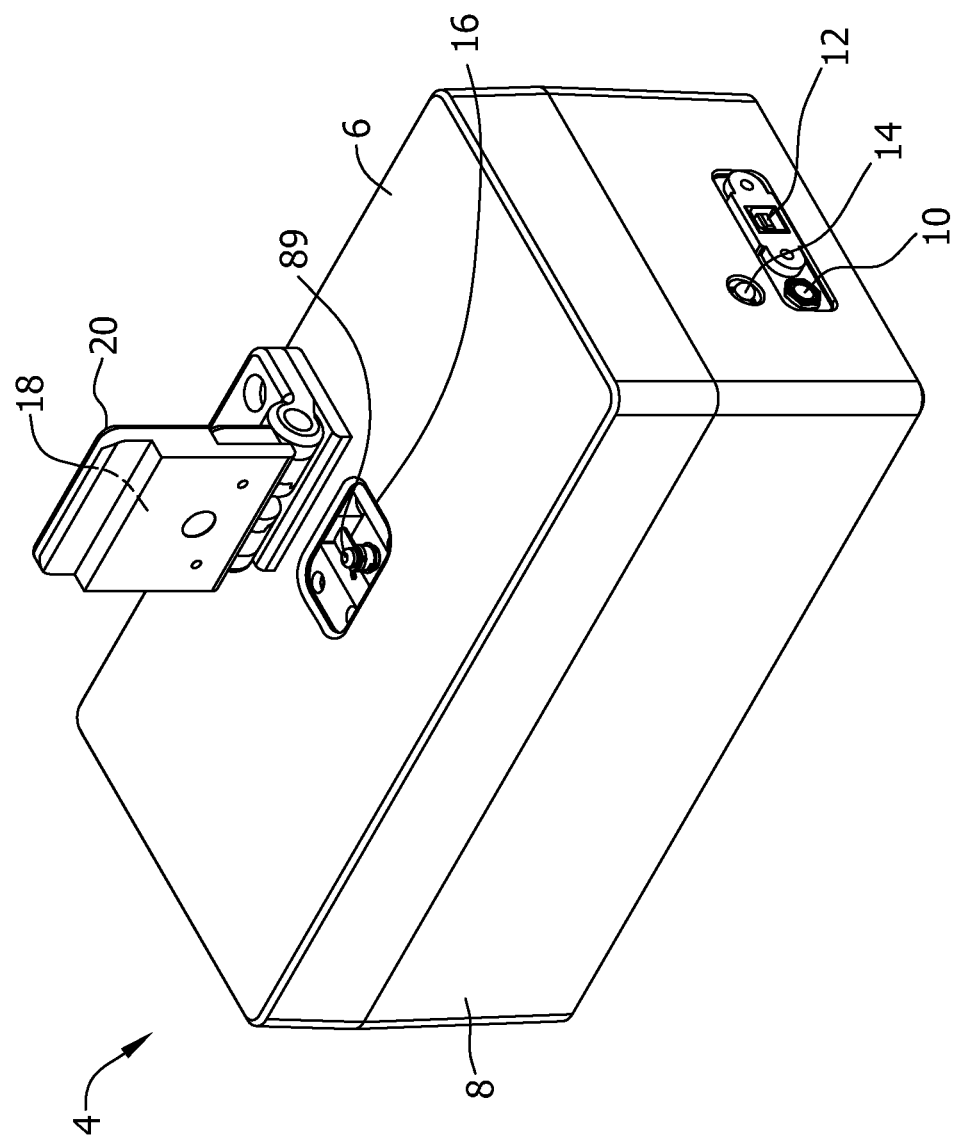
FIG. 2 is a perspective view of the portable system showing the hinged cover open.
Figure 3:
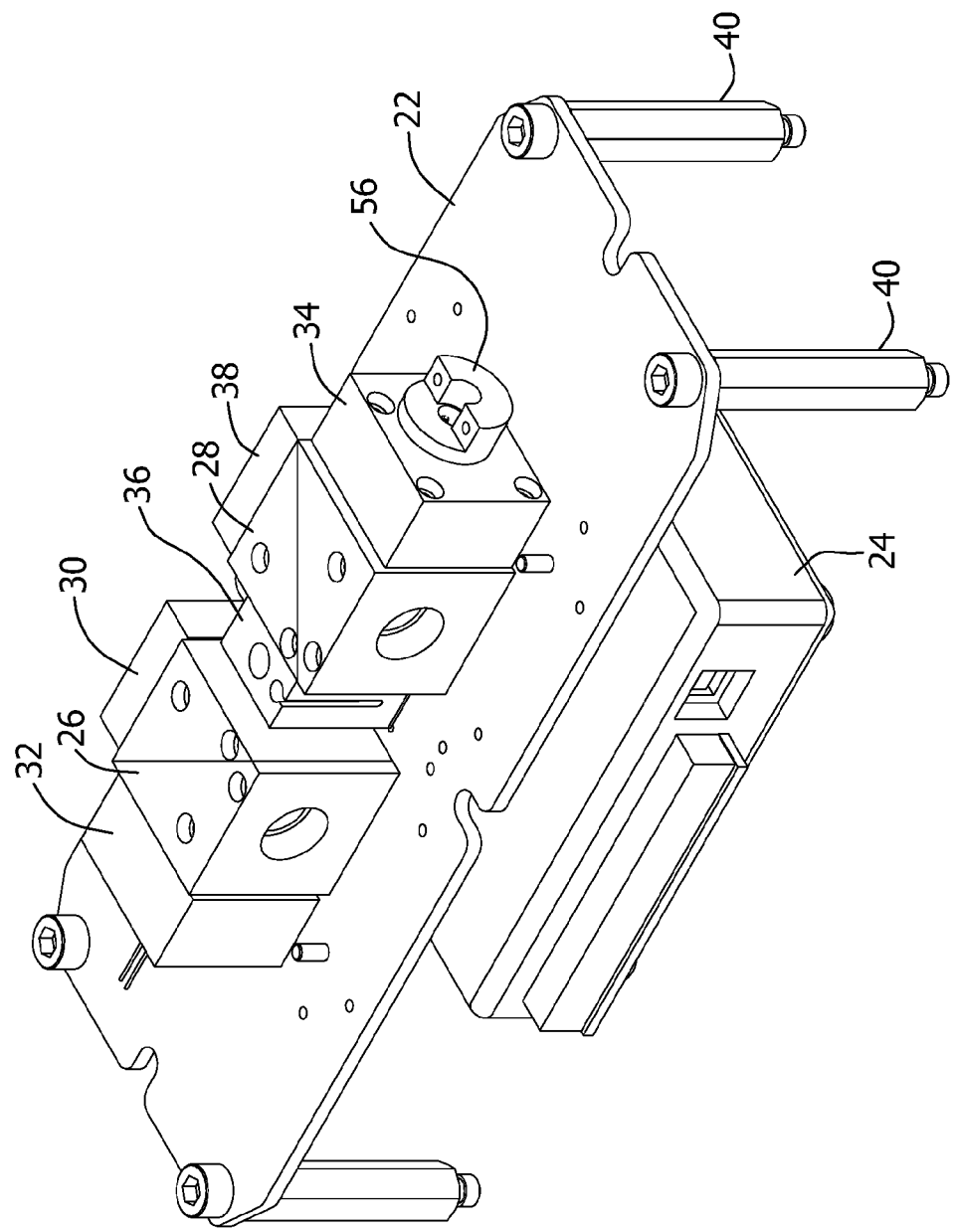
FIG. 3 is an enlarged perspective view of the portable system with the lid and system housing omitted for clarity.

A portable system constructed in accordance with the provisions of the present disclosure is generally shown in FIGS. 1-2, with the system being generally referenced as numeral "4." The system 4 (synonymously "instrument") is shown in FIGS. 1 and 2 as having a lid 6 and system housing 8 and is shown in FIG. 3 with the lid and housing removed for purposes of illustration. The system 4 includes a power port 10 and data port 12 for connecting the system to a processing unit (e.g., computer) and a power indicator light 14 that indicates whether the system is under power. The power port 10 may be attached to a power supply (not shown). Optionally the system may be powered by a battery pack (not shown) for mobile application. The lid 6 and system housing 8 may be constructed of materials that are suitable for use in portable systems including, without limitation, metals (e.g., aluminum), thermoplastic polymers or coated thermoplastic polymers.

The lid 6 includes a hinged port cover 18 that covers a sample access port 16 (FIG. 2). The access port 16 allows for removable (or temporary) placement of a sample vial 89 into the system 4 for analysis. The cover 18 has a lip 20 that extends outward such that the user may easily open and close the cover. The cover 18 may be removably attached to the lid 6, such as by friction fitting with the port 16, by hook and loop fasteners, or other suitable ways.

Figure 4:
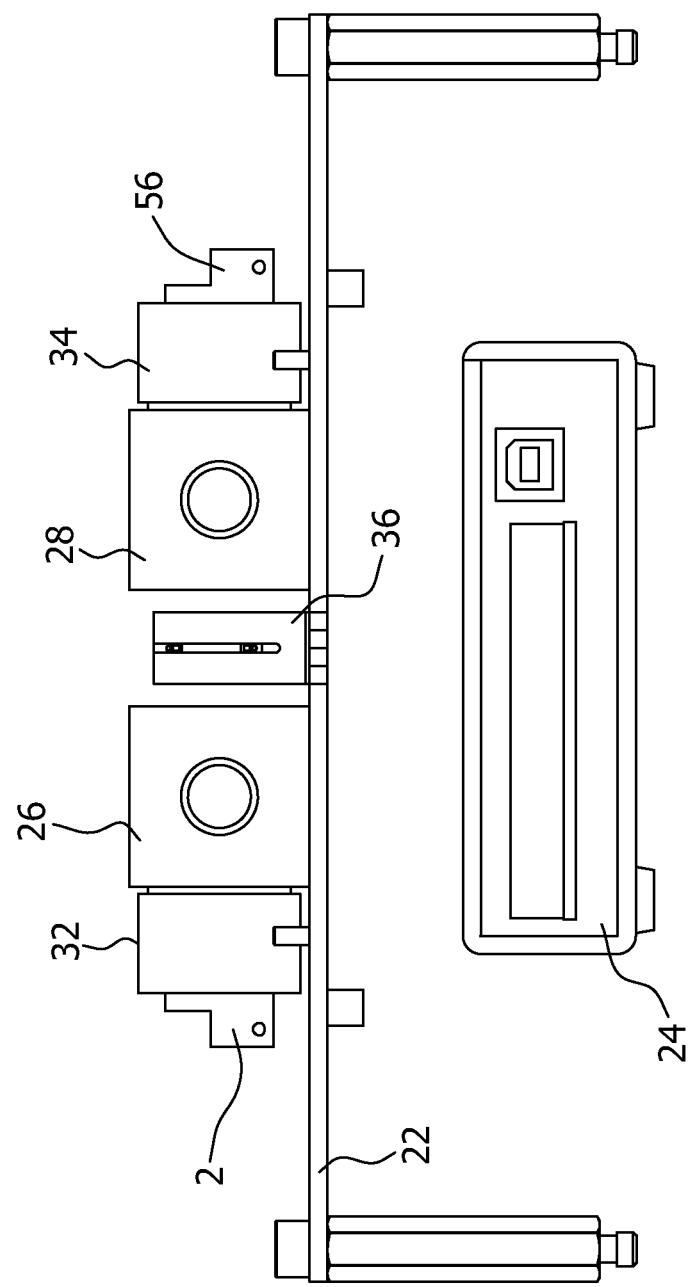
FIG. 4 is a front view of the portable system with the lid and system housing not shown.

Referring now to FIG. 3, the system includes a mounting plate 22 and data acquisition unit 24. The data acquisition unit 24 provides digital input and outputs and may interface with a processor (i.e., computer) via data port 12 (FIG. 2). Attached to the mounting plate 22 are a first optics module housing 26, a second optics module housing 28, a first lens housing 32, a second lens housing 34, a sample module housing 36, a first light source housing 30 and a second light source housing 38. The mounting plate 22 is attached to supports 40 that may be attached to the bottom of the system housing 8 (FIG. 1). As seen in FIG. 4, the system also includes a first detector housing 2 and a second detector housing 56. Electrical circuit boards (not shown) in electrical contact with the detectors within the housings 2, 56 may be attached to the housings.

Figure 5:
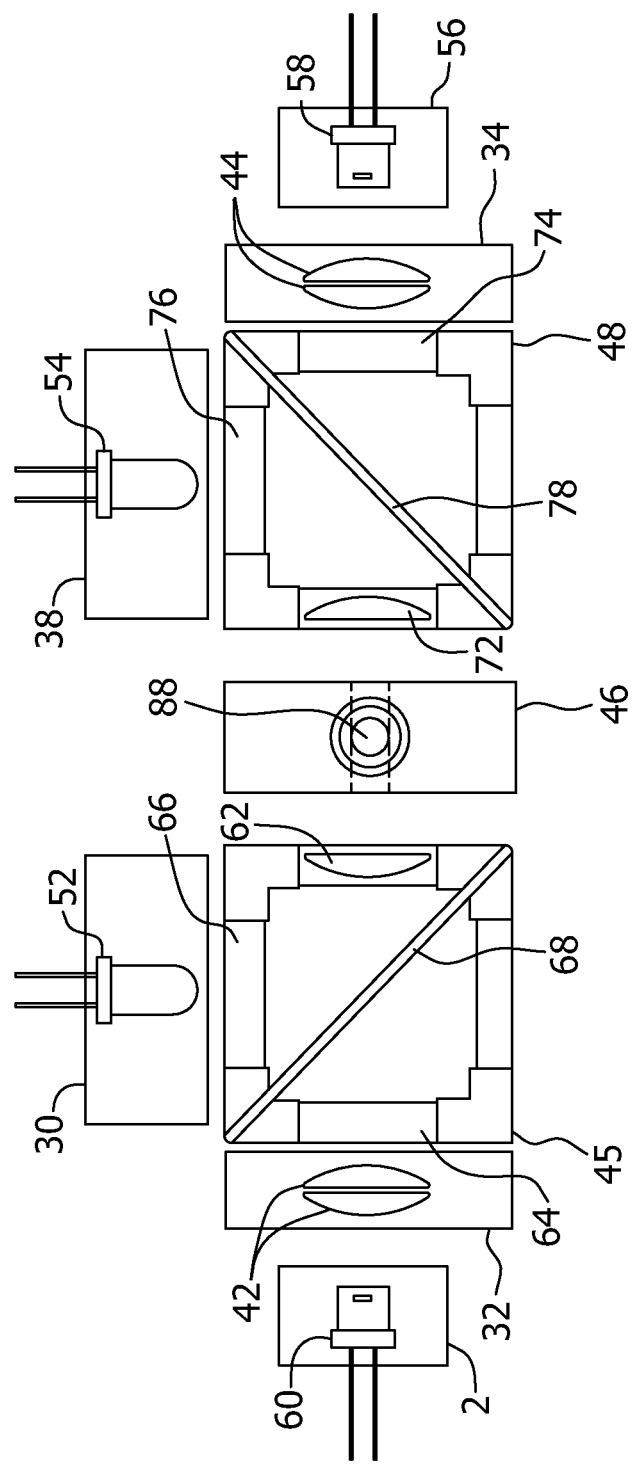
FIG. 5 is a partial schematic top view of the system.

A partial view of the system 4 is shown in a top-view schematic in FIG. 5. It should be noted that this figure is not drawn to scale. The system includes a first optics module 45, a second optics module 48, a third lens 42, a fourth lens 44, a sample module 46, a first light source 52 and a second light source 54. Generally, these parts are held by or within their respective housing elements which are shown in (FIGS. 3-4). It should be noted that the third lens 42 is held within the first lens housing 32 and the fourth lens 44 is held within the second lens housing 34, respectively. A sample 88 is held in the sample module 46.

The first optics module 45 includes a first excitation filter 66, a first lens 62, a first dichroic mirror 68 and a first emission filter 64. The second optics module 48 includes a second excitation filter 76, a second lens 72, a second dichroic mirror 78 and a second emission filter 74. In operation of the system, the first light source 52 and second light source 54 may be powered alternately (and in some embodiments simultaneously) to detect fluorescence omitted by fluorophores in the reaction sample 88 held by the sample module 46. It should be noted that the system 4 as described herein is arranged such that the first detector 60 detects light emitted from the sample 88 in response to light absorbed from the first light source 52 and the second detector 58 detects light emitted from the sample 88 in response to light absorbed from the second light source 54. In this regard, it should understood that the sample 88 emits light in the direction of both detectors 58 and 60 in response to excitation light and that the system 4 may alternatively be arranged such that the first detector 60 detects light emitted from the sample 88 in response to light absorbed from the second light source 54 and the second detector 58 detects light emitted from the sample 88 in response to light absorbed from the first light source 52.

The excitation filters 66, 76 and emission filters 64, 74 filter out stray light so as to allow light of a specific wavelength (or band of wavelength) to pass. Suitable filters may be made of, for example, glass housed in black-anodized aluminum rings and are commercially available from Semrock, Inc. (Rochester, N.Y.). The dichroic mirrors 68, 78 reflect a narrow wavelength range of light and let other wavelengths pass through the mirror. The dichroic mirrors 68, 78 reflect light about 90°; however, it should be understood that other degrees of reflection may be used without limitation. Reflection of light off the dichroic mirrors 68, 78 allows only scattered light emitted by the sample to reach the detectors 60, 58. Light that passes through the dichroic mirrors 68, 78 (e.g., light that passes from the first light source 52 and through the dichroic mirror 68) may pass through a light port (designated as 71 in the first optics module 45 shown in FIG. 11) out of the optics modules 45, 48 so as to not be redirected toward the sample 88 or to the detectors 60, 58. The light that passes through the light port 71 may be absorbed by the inner surface of the system housing 8 (FIG. 1). This inner surface may be coated with dark paint and/or anodized to facilitate absorption of light.

The dichroic mirrors 68, 78 also allow light emitted from the sample 88 (which is of a different wavelength than light emitted than the light source) to pass through without reflection. For instance, light emitted from the sample 88 as a response to light absorbed from the first light source 52 may pass through the first dichroic mirror 68 and toward the first detector 60 and light emitted from the sample 88 as a response to light absorbed from the second light source 54 may pass through the second dichroic mirror 78 and toward the second detector 58. The first and second lenses 62, 72 focus light toward the sample 88 held in the sample module 46. The third and fourth lenses 42, 44 focus light toward the first and second detectors 60, 58. The first and second lenses 62, 72 are shown as being bi-convex and the third and fourth lenses 42, 44 are shown as plano-convex. This arrangement has been found to result in improved depth of field and focal lengths; however, it should be understood that other arrangements (specifically, the selection of bi-convex or plano-convex lenses) may be used without departing from the scope of the present disclosure.

Figure 6:
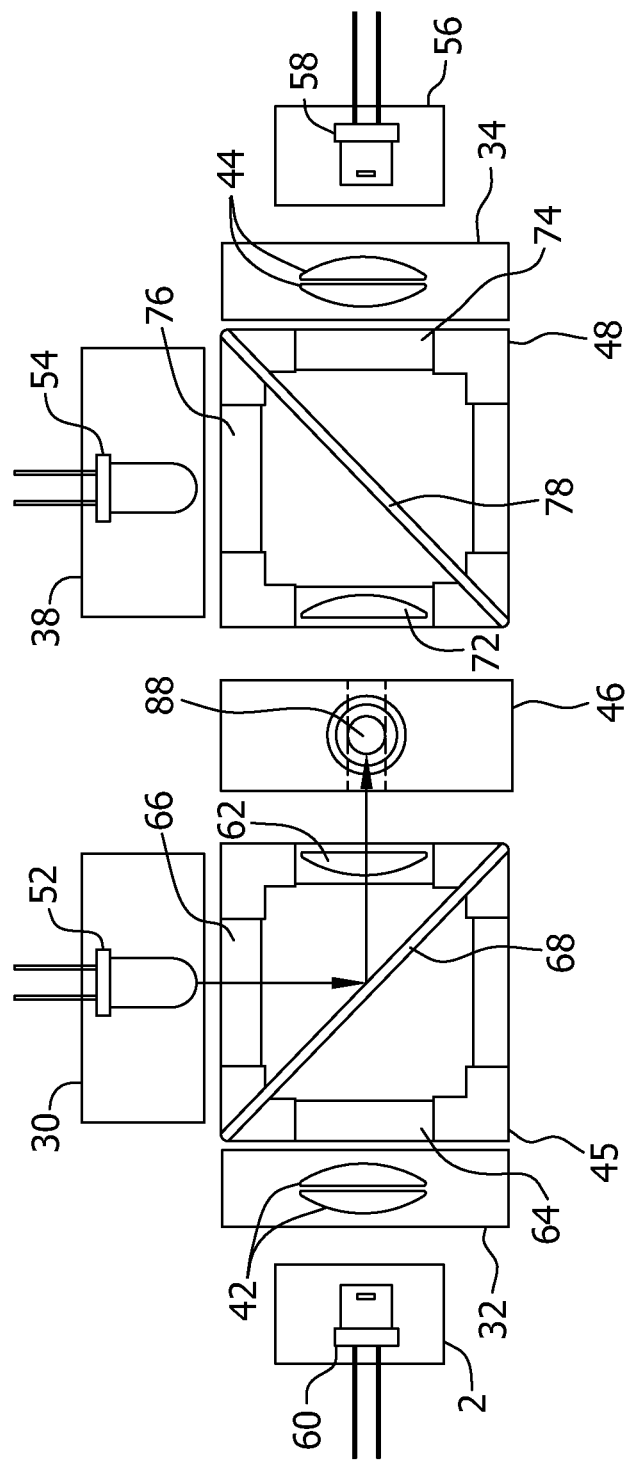
FIG. 6 is a partial schematic top view of the system with the pathway of light emitted from a first light source to a sample shown.
Figure 7:
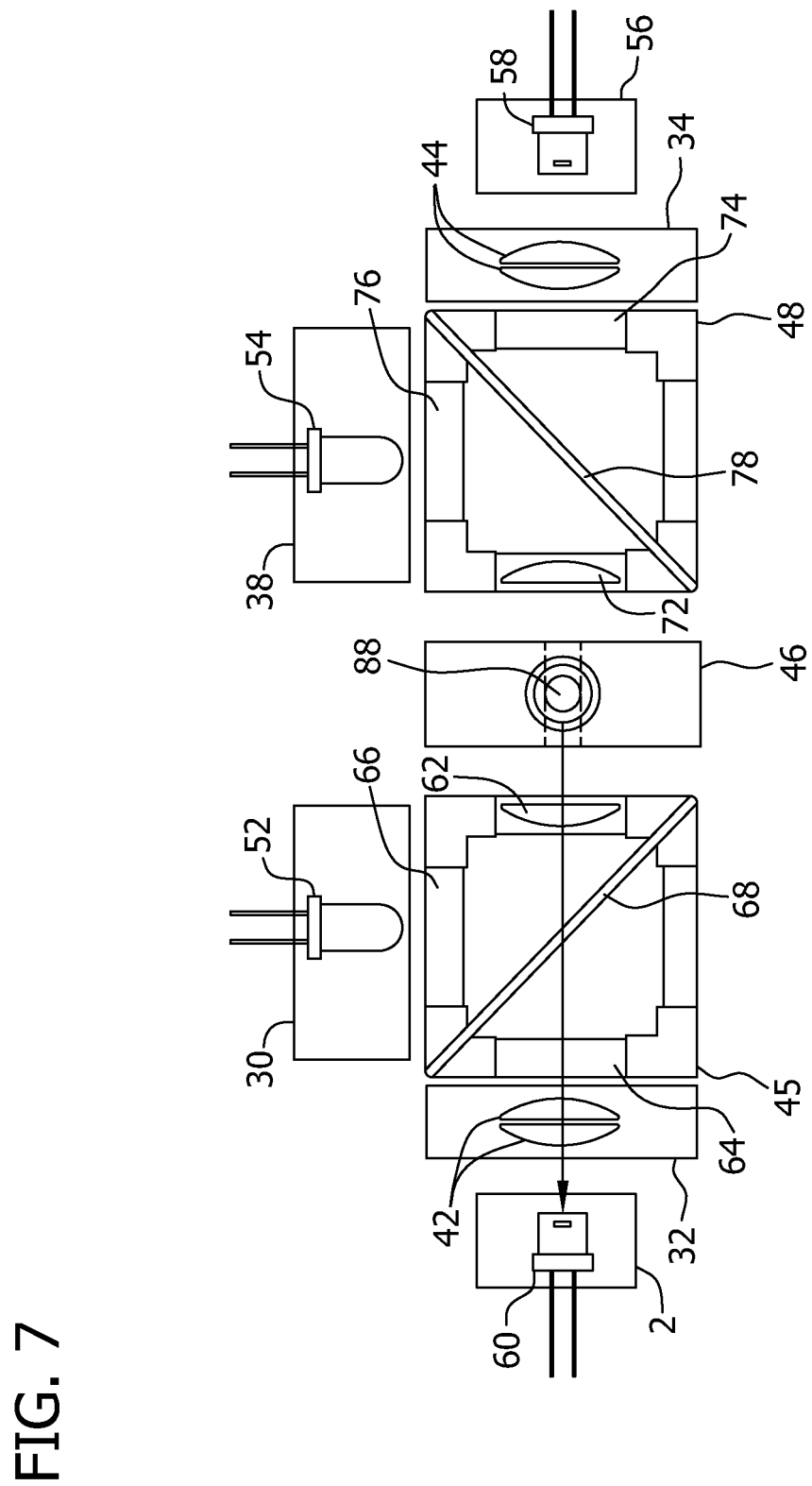
FIG. 7 is a partial top view of the system with the pathway of light emitted the sample to a first detector shown.
Figure 8:
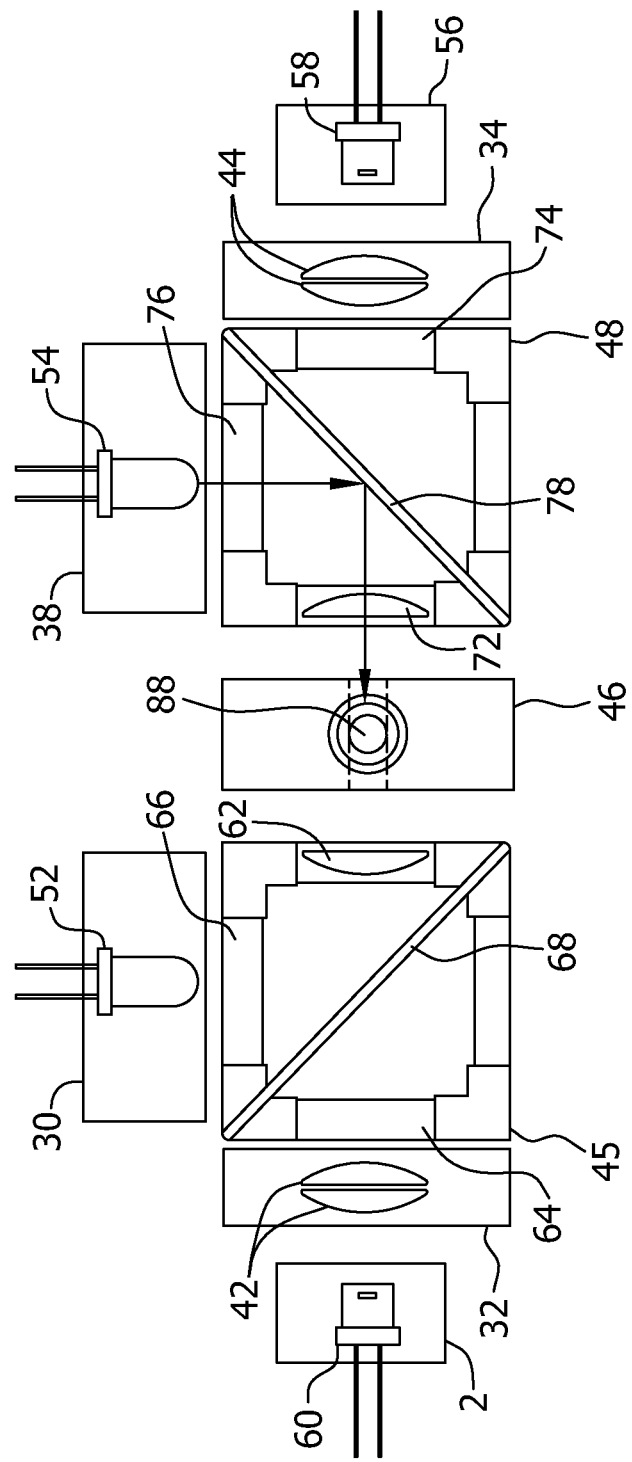
FIG. 8 is a partial schematic top view of the system with the pathway of light emitted from a second light source to the sample shown.
Figure 9:
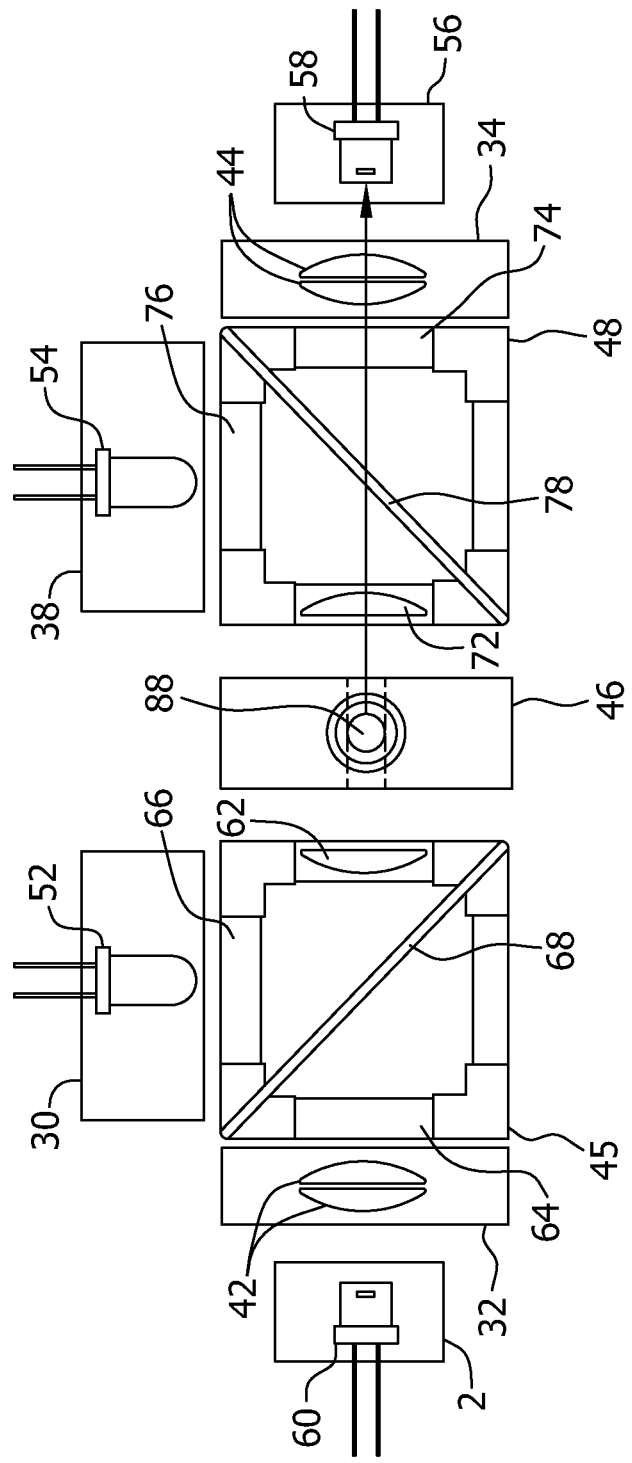
FIG. 9 is a partial top view of the system with the pathway of light emitted the sample to a second detector shown.

The light emitted by the first light source 52 travels to the sample 88 and light emitted from the sample in response to this light travels to the first detector 60 along a first optical pathway. The light emitted by the second light source 54 travels to the sample 88 and light emitted from the sample in response to this light travels to the second detector 58 along a second optical pathway. The parts of the system 4 in which the optical pathways extend are generally referred to as a first optics channel and a second optics channel, respectively. As shown in FIGS. 6-7, the first optics channel includes the first excitation filter 66, the first dichroic mirror 68, the first lens 62, the first emission filter 64 and the third lens 42. As shown in FIGS. 8-9, the second optics channel includes the second excitation filter 76, the second dichroic mirror 78, the second lens 72, the second emission filter 74 and the fourth lens 44.

Figure 10:
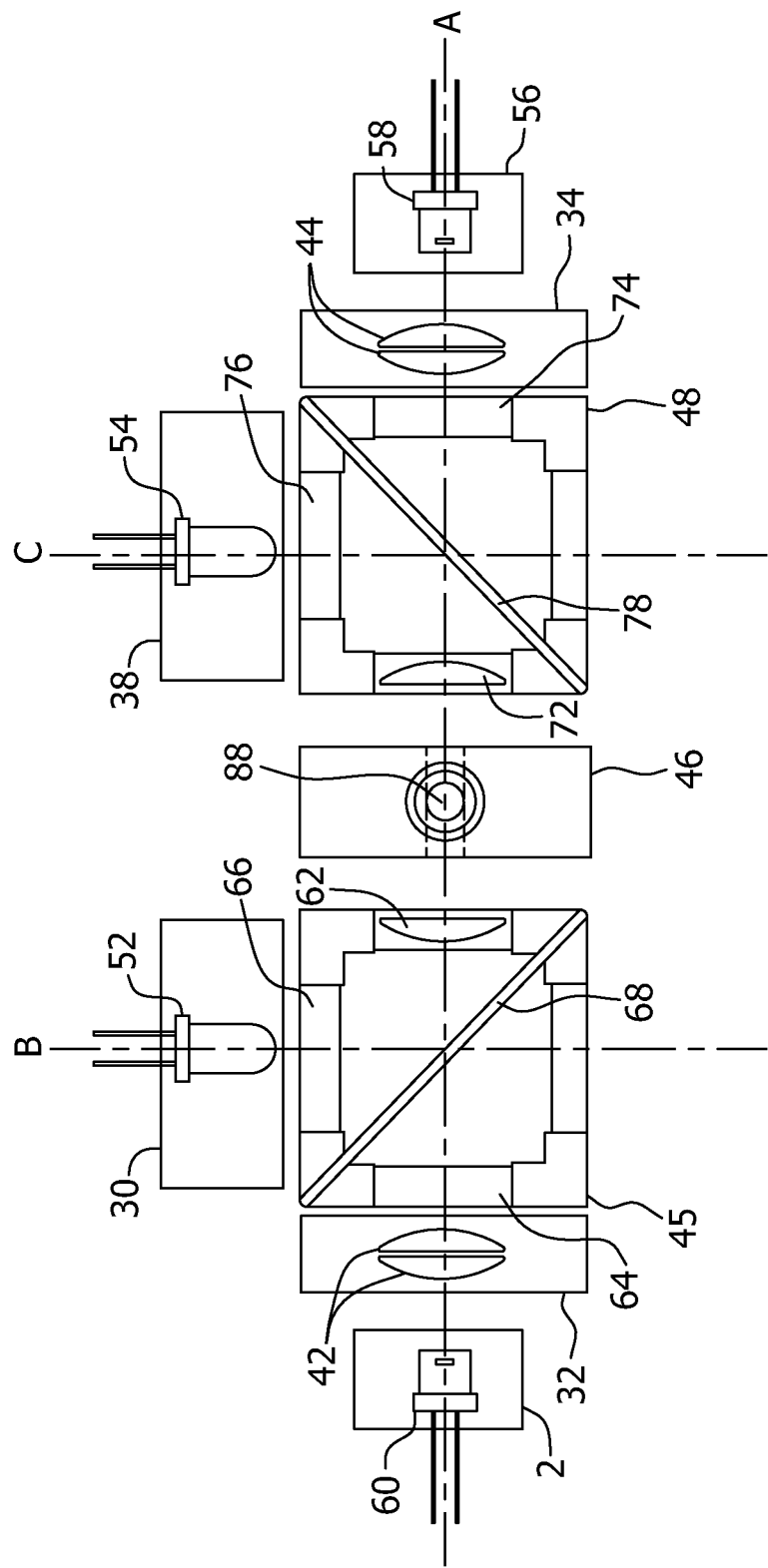
FIG. 10 is a partial schematic top view of the system illustrating several planes which intersect the various parts of the system.

As can be seen from FIG. 10, the first and second detectors 60, 58; first, second, third and fourth lenses 62, 72, 42, 44; first and second emission filters 64, 74; and first and second dichroic mirrors 68, 78 are all intersected by a first plane designated as plane A. The first light source 52, first excitation filter 66 and first dichroic mirror 68 are intersected by a second plane designated as plane B. The second light source 54, second emission filter 76 and second dichroic mirror 78 are intersected by a third plane designated as plane C. The plane generally formed by the first light source 52 and the first dichroic mirror 68 and the plane formed by the second light source 54 and the second dichroic mirror 78 are generally perpendicular to the plane generally formed by the two detectors 60, 58.

Figure 11:
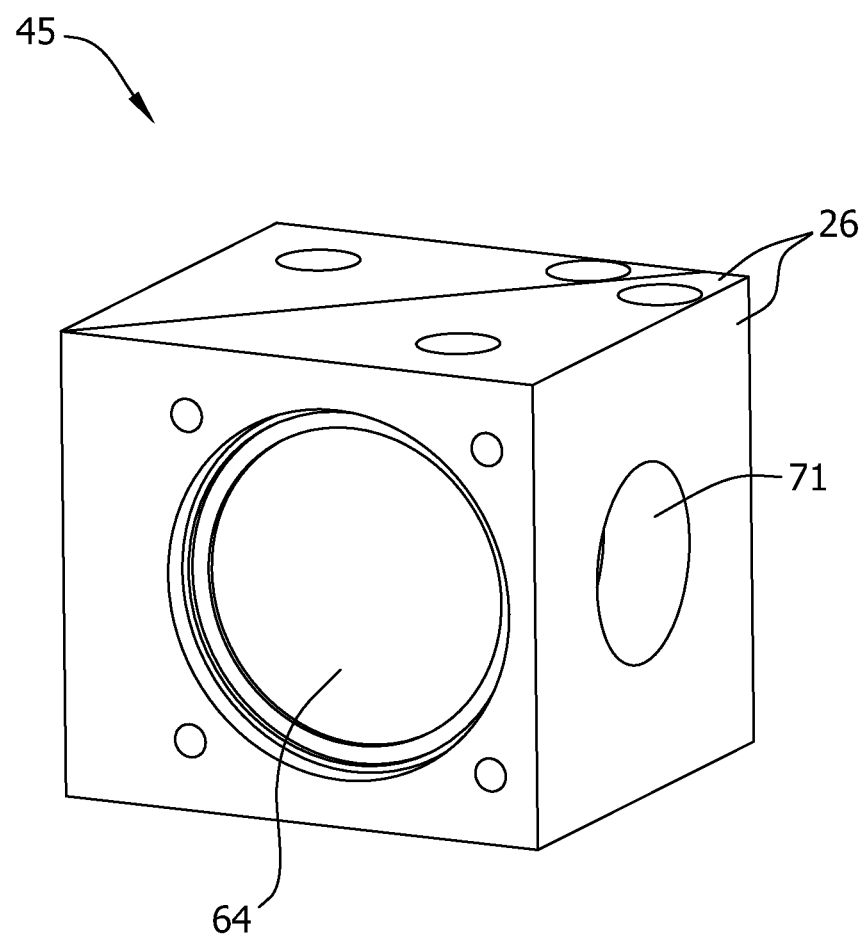
FIGS. 11-13 are perspective views of an optics module.
Figure 12:
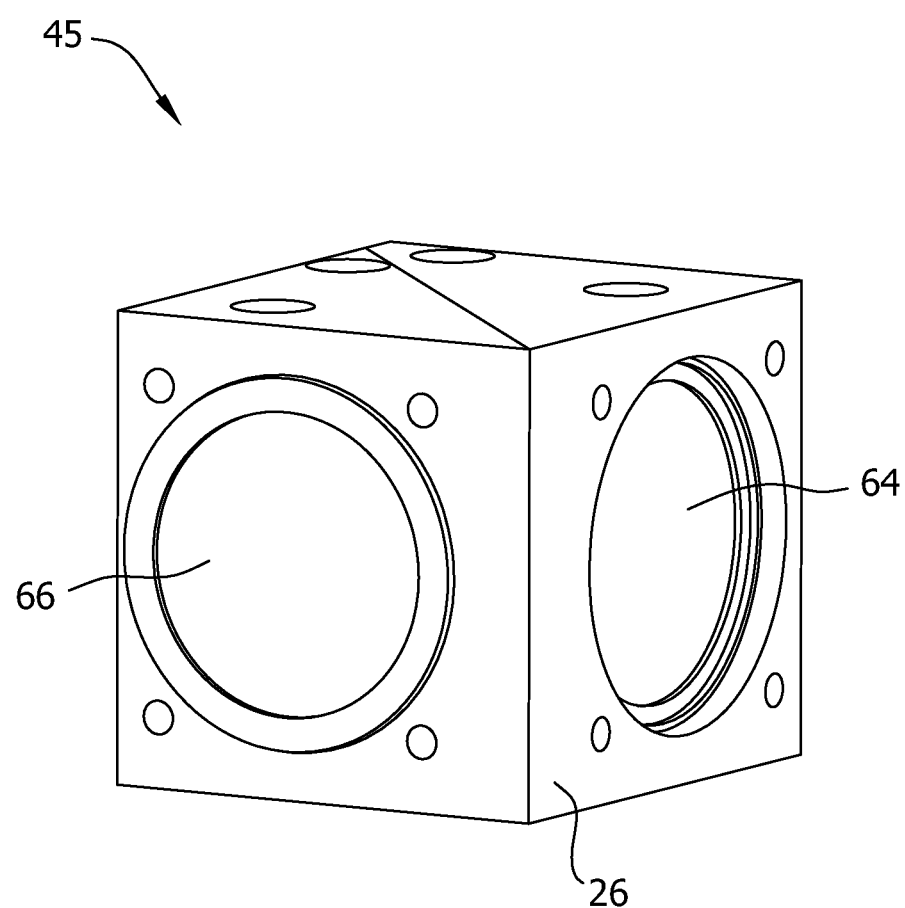
Figure 13:
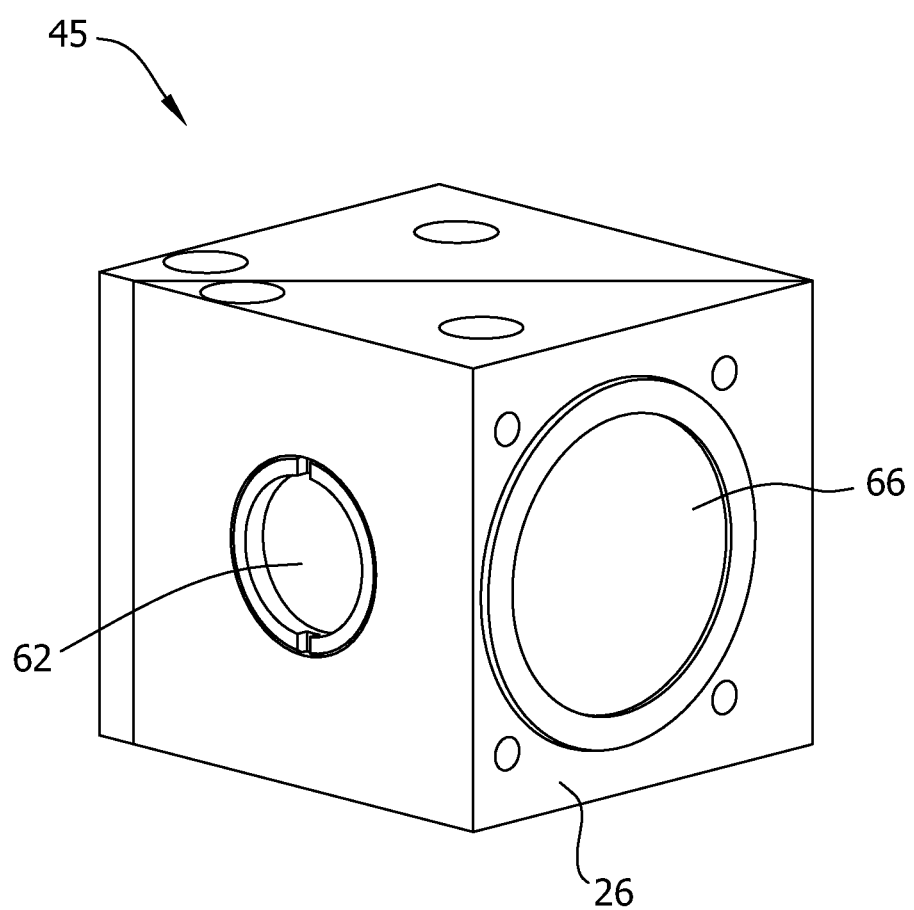
Figure 14:
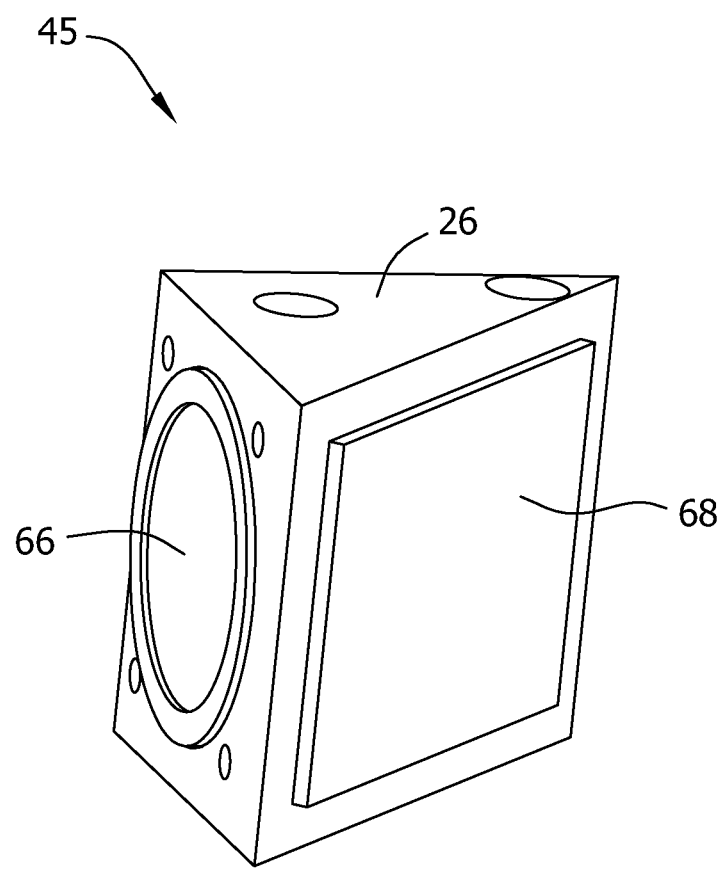
FIG. 14 is a perspective view of the optics module with one half of the module not shown to illustrate the dichroic mirror.

Referring now to FIGS. 11-14, the first optics module 45 includes a first optics module housing 26. The housing 26 supports a first emission filter 64 (FIG. 11), first excitation filter 66 (FIG. 12) and first lens 62 (FIG. 13). A first light port 71 may also be formed in the housing 26 (FIG. 11). A portion of the housing 26 is removed in FIG. 14 to show the first dichroic mirror 68 which is supported by the housing 26. The second optics module 48 is similar to the first optics module 45; however the parts of the second optics module are arranged as shown in FIGS. 5-9.

Figure 15:
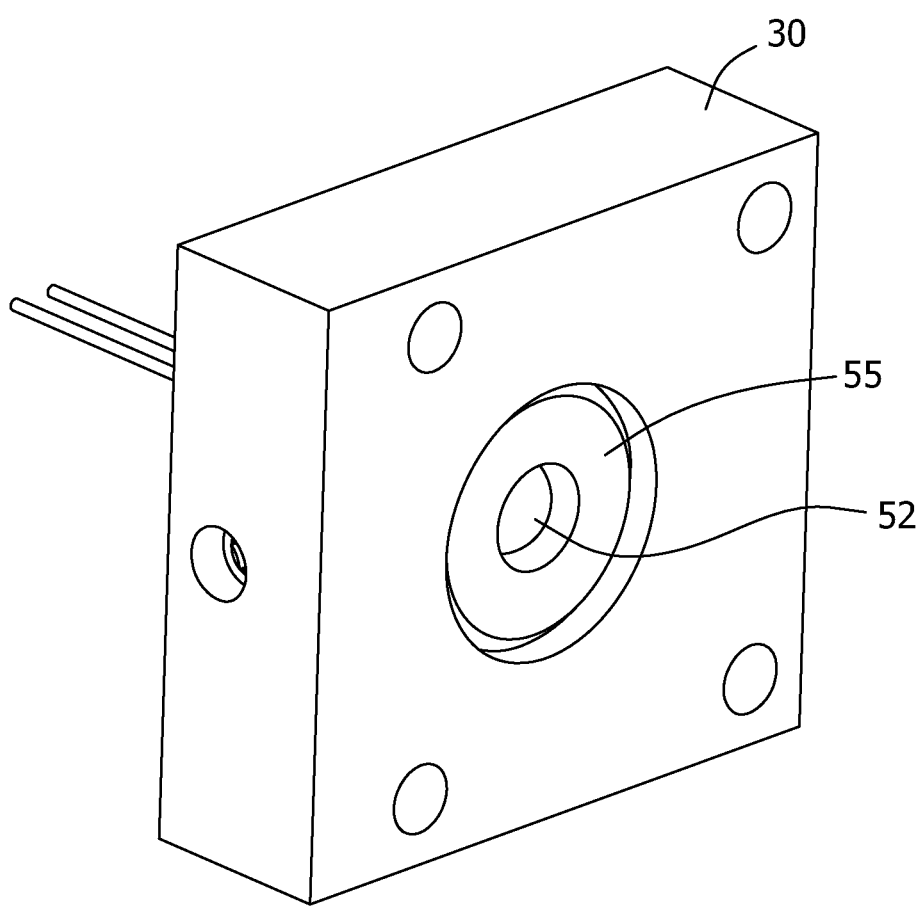
FIG. 15 is a perspective view of a light source and its housing.
Figure 16:
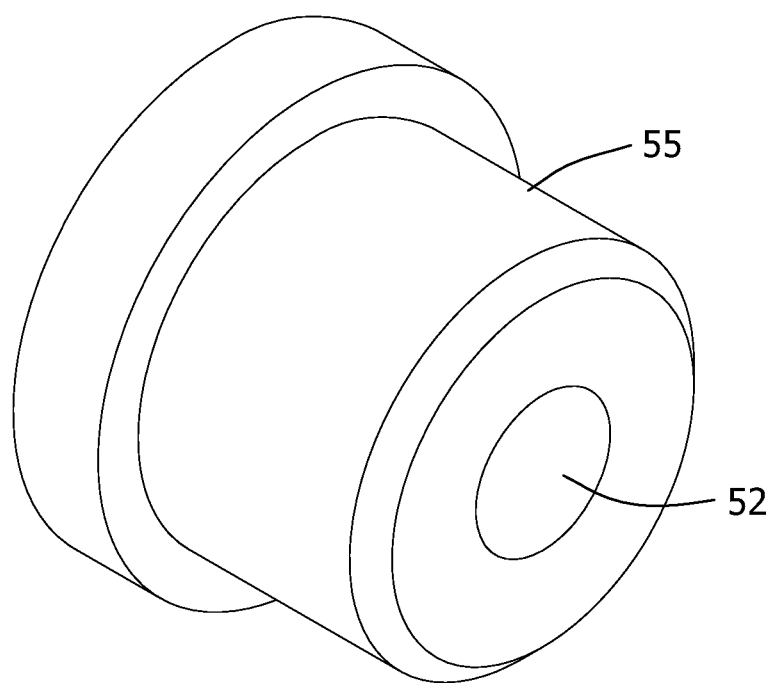
FIG. 16 is a perspective view of a light source collet with the light source housing removed.

The first light source 52 and first light source housing 30 may be seen in FIG. 15. The first light source 52 is secured within a first light source collet 55. The first light source 52 and collet 55 are shown with the housing removed in FIG. 16. The first and second light sources 52, 54 may be lasers or light emitting diodes ("LEDs"). Preferably the light that is emitted is of a specific wavelength (as with lasers and LED devices) or is filtered to emit a specific wavelength (as with monochromators). In some embodiments, the first light source 52 and second light source 54 emit light of different wavelengths.

Figure 17:
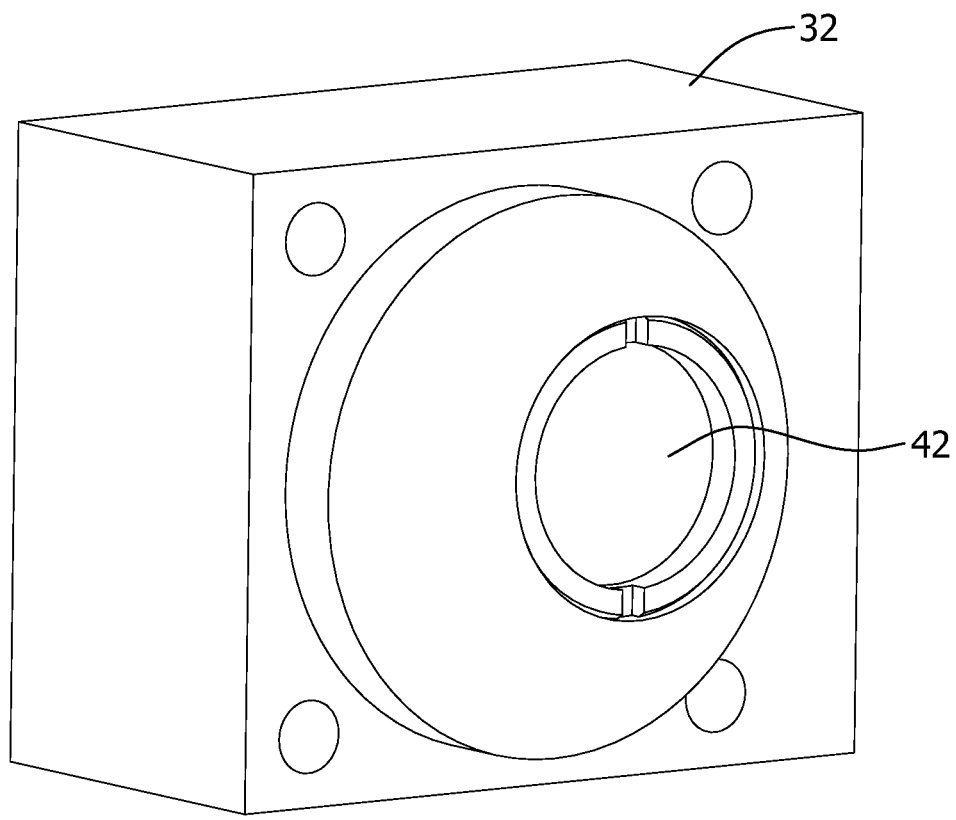
FIG. 17 is a perspective view of a lens and its housing.
Figure 18:
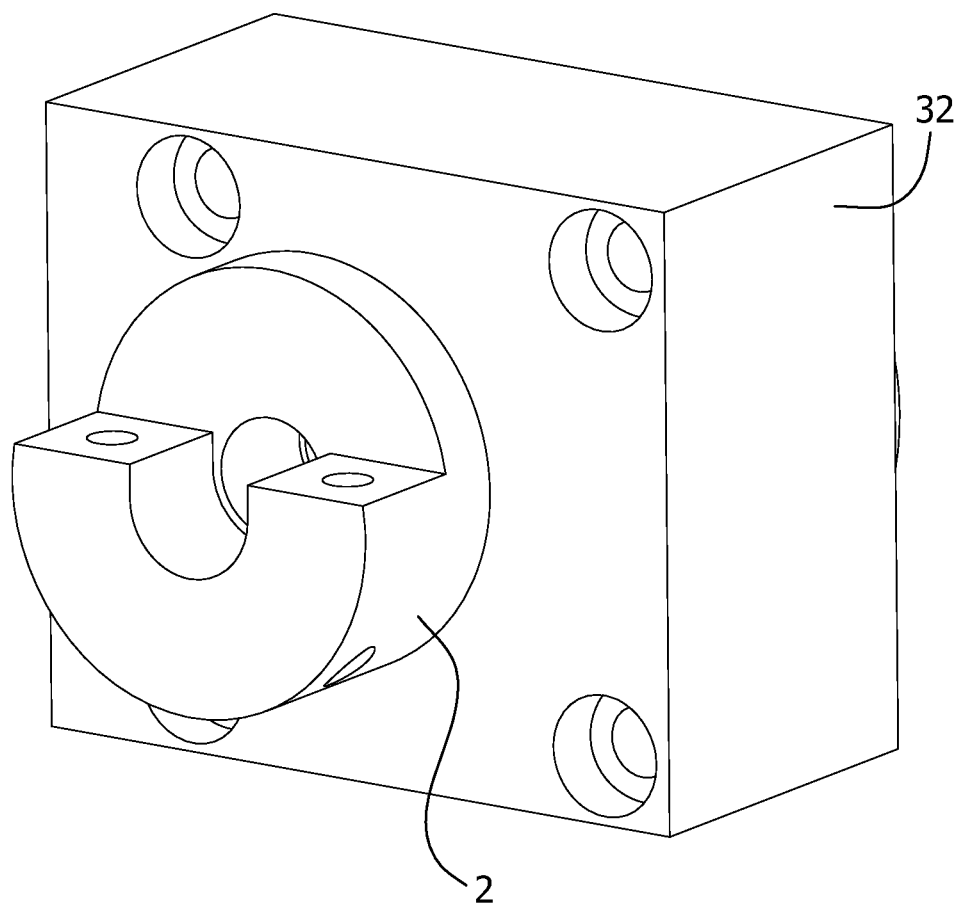
FIG. 18 is a perspective view of the lens housing and a fluorescence detector housing.
Figure 19:
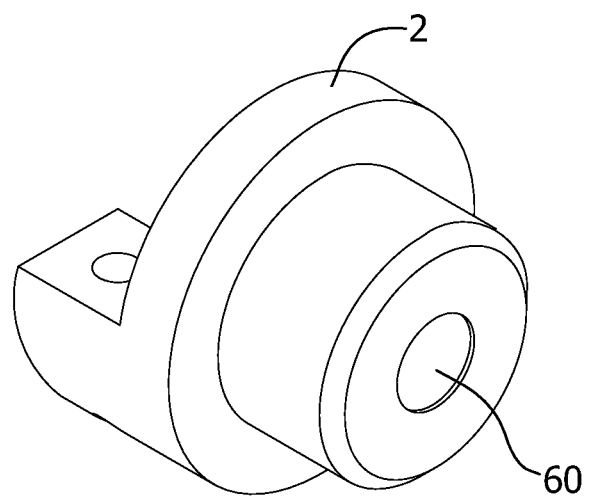
FIG. 19 is a perspective view of the detector and its collet.

The third lens 42 and first lens housing 32 are shown in FIG. 17. The fourth lens 44 and second lens housing 34 are similar to the third lens 42 and first lens housing 32. As can be seen in FIGS. 18 and 19, the first detector housing 2 that secures the first detector 60 fits within the first lens housing 32.

Figure 20:
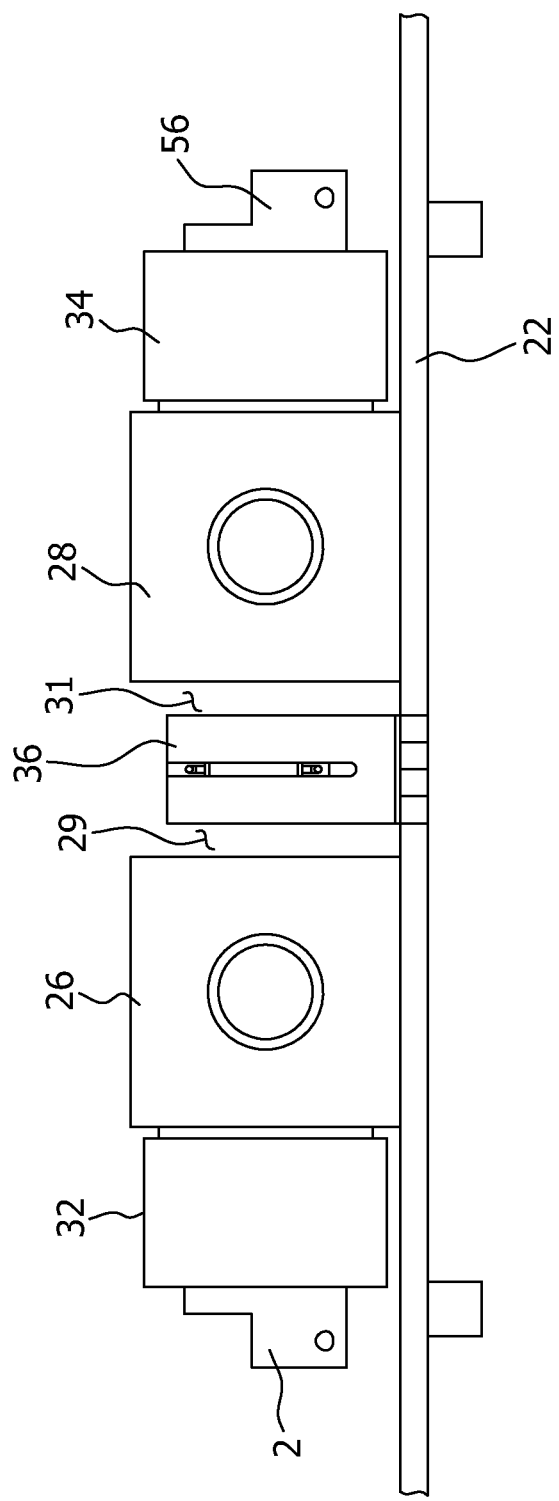
FIG. 20 is a front view of the portable system with the lid and system housing not shown.

Referring now to FIG. 20, the sample module housing 36 is separated from the first optics module housing 26 by a first space 29 and is separated from the second optics module housing 28 by a second space 31. This arrangement allows the sample module to undergo mixing operations without affecting the operation of the optics. The first space 29 and second space 31 prevent movement (e.g., vibration) of the sample 88 and sample module housing 36 from translating to the first optics module housing 26 and second optics module housing 28. The distance between the sample module housing 36 and the first optics module housing 26 and the second optics module housing 28 is not critical; however, the distance should be sufficiently small to allow light to pass from the first and second optics modules to the sample and from the sample to the first and second detectors and should be sufficiently large to allow sample mixing operations to not interfere with operation of the optics. Generally, distances of from about 100 µm to about 10 mm are suitable.

Figure 21:
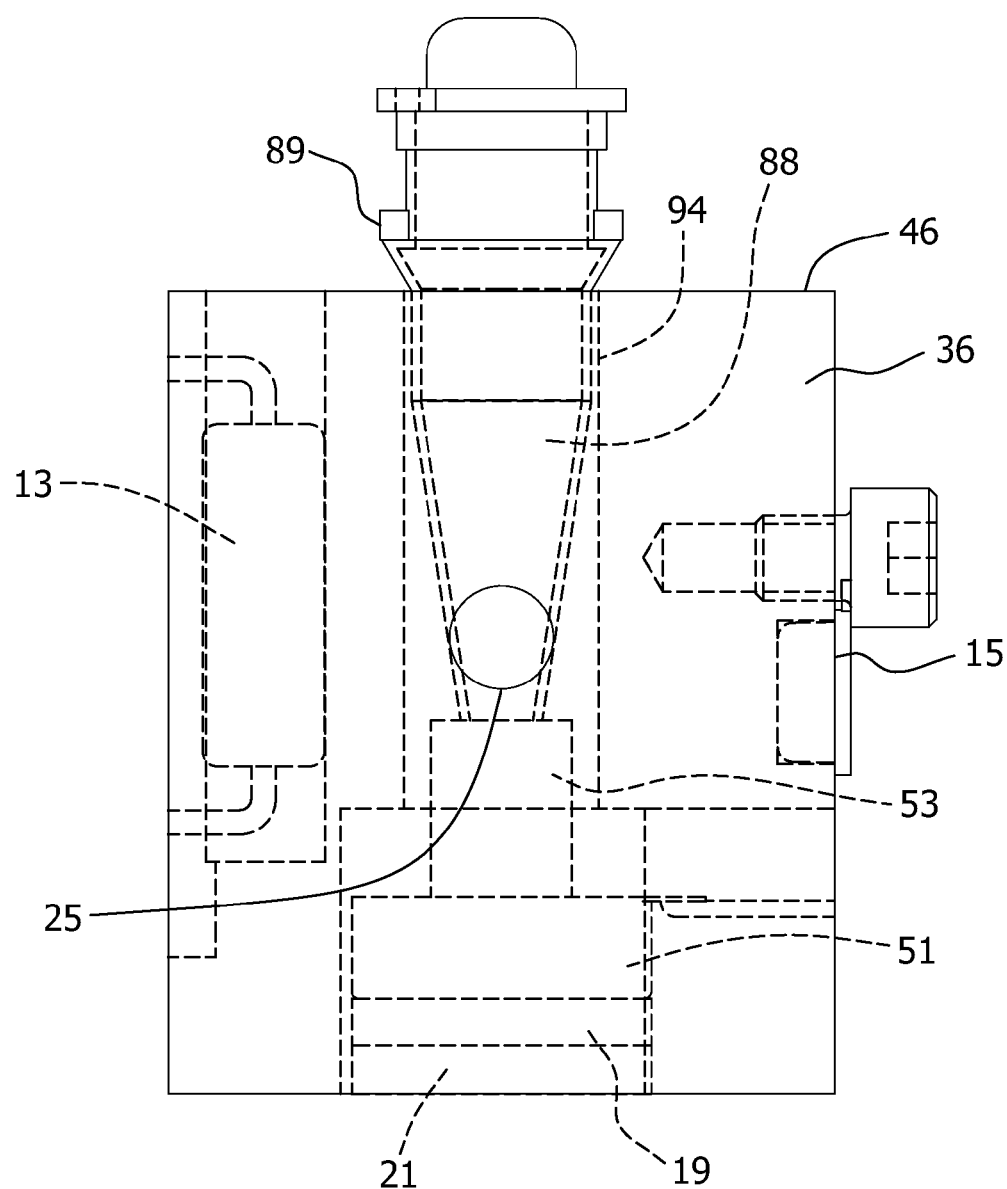
FIG. 21 is a right side view of a sample module and a reaction vial received therein.

A side view of the sample module 46 in transparent with a sample vial 89 received therein is shown in FIG. 21. The sample module 46 includes a chamber 94 into which the sample vial 89 is received. The sample module 46 includes a heating element 13 within the housing 36. The heating element 13 transfers heat to the sample 88 (synonymously "incubates" the sample) such that DNA amplification may occur more rapidly. Methods for heating include, for example, capacitive heating, induction coils and electrical resistance elements; however, other methods of heating may be used without limitation. The sample module 46 also contains a temperature sensor 15 for controlling the temperature of the sample 88. Suitable temperature sensors may be solid-state devices that produce a voltage that corresponds to the temperature within the sample module 46. The sample module 46 includes a first access port 25 and a second access port (not shown) opposite the first port in the housing 36 to allow light to pass in and out of the housing.

As seen in FIG. 21, the sample module 46 and the system 4 in general is configured to analyze only one sample (i.e., the system only has one sample module that is capable of receiving one sample vial). This allows the system to be portable as compared to conventional systems. Further, this allows the system to be simpler in design and in operation which minimizes the cost of the system and the need for highly trained personnel to operate the system. In this regard, it should be understood that in certain embodiments, the system may allow for analysis of multiple samples (FIG. 23) as explained below.

The sample module 46 includes a vibratory motor 51 and a solid coupling 53 that is attached to the vibratory motor and is capable of receiving the sample vial 89. The vibratory motor 51 may be attached to the solid coupling 53 by any of the methods known in the art such as, for example, adhesives or by threading the coupling to the motor. By applying power to the vibratory motor 51, vibrations translate to the solid coupling 53 and to the vial 89 received in the coupling and to the sample 88.

A vibratory insulating spacer 19 is attached to the motor 51. The vibratory insulating spacer 19 absorbs vibrations from the motor 51 which prevents the vibrations from traveling to the mounting plate 22 (FIG. 4) during operation of the vibratory motor. This prevents vibration of the mounting plate 22 and of the first and second optical modules 45, 48. The vibratory insulating spacer 19 is attached to a second spacer 21 to reduce the height of the solid coupling 53 and, in this manner, the mass of the solid coupling. In this regard, the mass of the solid coupling 53 may be selected to be within a range that is suitable for use with the vibratory motor 51 as may be determined by those of skill in the art (for example, by experimentation with various coupling weights).

Figure 22:
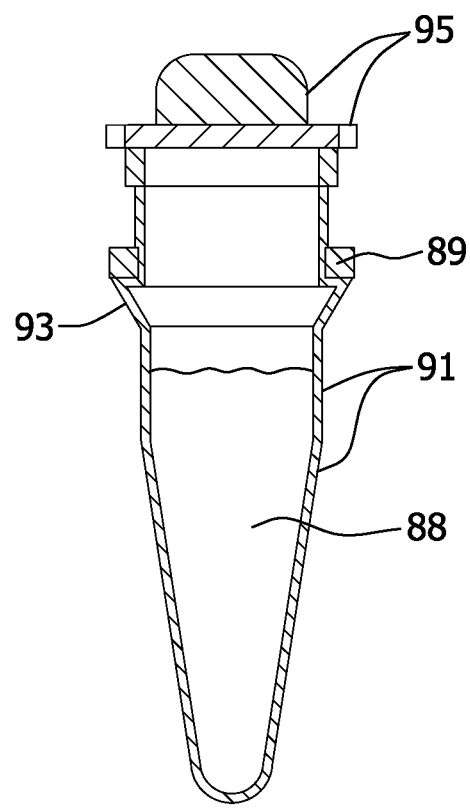
FIG. 22 is a side view of a reaction vial suitable for use in the portable system.

An exemplary reaction vial 89 is shown in FIG. 22. The vial 89 includes a sample 88 for analysis therein. The vial 89 includes a well portion 91 and a flared portion 93 for seating the vial into the sample module 46 (FIG. 21). The vial 89 includes a resealable cap 95 for sealing the vial. Generally, the cap 95 is friction-fit within the vial 89 for sealing. The cap may be hinged to keep the cap attached to the vial 89 when open. A user may apply an opening force to the cap so as to unseat the friction-fitting cap 95 so as to open the vial. It should be understood that other types of vials with differing features may be used without departing from the scope of the present disclosure. In this regard, the vial 89 generally does not form part of the system 4 as suitable vials may be readily obtained commercially.

Generally, the parts described above may be made of any material suitable for fluorometry operations. In various embodiments, the parts are durable to withstand portable applications including field use of the system. The housing materials may suitably be constructed of thermoplastics or of machined aluminum and may be non-reflective (i.e., light absorbing). Aluminum is known to scatter light which may impact signal detection, thus it is preferred that aluminum parts be coated with a dark paint and/or be anodized. Emission and excitation filters and lenses are available commercially and may be readily chosen by those of skill in the art. For example, the excitation filters may be selected to pass a maximum amount of energy that is in the excitation band to the sample and to attenuate energy in the emission ranges.

The system described above and shown in FIGS. 1-22 is capable of both amplifying nucleotide and detecting two or more nucleotide sequences. While reference is made herein to detection of DNA sequences and DNA amplification, it should be understood that the systems and methods described herein are also suitable for RNA detection and RNA amplification and references to the detection and/or amplification of DNA should not be viewed in a limiting sense. Generally, the system uses RPA amplification techniques; however it should be understood that PCR and/or other isothermal amplification methods may be used without departing from the scope of the present disclosure. RPA amplification is generally described in U.S. Pat. No. 7,270,981 which is incorporated herein for all relevant and consistent purposes.

In accordance with the present disclosure, the portable system is capable of detecting two sequences of DNA of a sample. In various embodiments, the sample in the sample vial contains amounts of two fluorophore probes. Each probe contains a fluorescent dye attached to a quencher. Suitable fluorophore dyes are known in the art and include TAMRA, FAM, ROX, HEX, JOE, Cy3, Cy5, TET and Texas Red. In some embodiments, tetramethylrhodamine ("TAMRA") and fluorescein ("FAM") are used as fluorophore dyes. The probe hybridizes to its target DNA sequence and enzymes present in the reaction cleave the probe which allows the fluorophore to fluoresce upon absorption of visible light.

The first light source 52, first fluorophore and first detector 60 are generally selected such that the first light source emits a wavelength of light that the fluorophore is capable of absorbing and the detector is designed to detect a wavelength of light the fluorophore emits. The second light source 54, second fluorophore and second detector 58 are similarly selected. In operation of the instrument, as DNA is amplified, the first optics system may be operated by powering the first light source 52. The light passes through the first optics module 46 and to the sample 88. Upon reaching the sample 88, the light has been filtered such that only light of a narrow band of wavelength reaches the sample. Fluorophore dye compounds (specifically a fluorophore that was chosen such that it fluoresces in response to light emitted from the first light source) that are separated from their quenchers fluoresce. This emitted light passes through the first optics module 46 and to the first detector 60. The second light source 54 may similarly be powered to cause a second fluorophore to fluoresce. This fluorescence may be an indication of the presence of a second DNA sequence.

Generally, the sample 88 is heated to amplify DNA more rapidly. In RPA systems, heating may be isothermal and cycling is not required. Suitably the sample may be heated from its initial temperature (i.e., room temperature or at sub-zero temperatures as low as about −100° C. when lyophilized reagents are used) to about 20° C., to about 30° C., to about 40° C., to about 50° C., to about 75° C. or even higher.

The sample 88 may be prepared by methods generally known in the art. Template DNA may be obtained from the plant of interest such as, for example, soybeans. The plant material may be ground and/or dried. The ground material may be contacted with a lysis buffer to lyse the cells of the plant material and expose template DNA. Typically, lysis buffers include, for example, sodium hydroxide, EDTA, SDS, tris-HCl and deoxycholate. The lysed material may be added to a rehydration buffer that acts to rehydrate the lyophilized reagents Once the lysed plant material has dissolved in the rehydration buffer, RPA reagents (optionally lyophilized) may be added (or PCR reagents as in some embodiments). RPA reagents may be lyophilized in the reaction vial 89 and the rehydrated lysed plant material added thereto. The RPA reagents generally include, without limitation, the fluorophore probes, nucleotides, DNA polymerase, primers, recombinase, DNA binding proteins, ATP, phosphocreatine, creatine kinase, crowding agents, recombinase loading agents and the like.

Once the template DNA and RPA reagents are added to the reaction vial 89 to form the reaction mixture, the hinged port cover 18 of the system 4 may be opened (FIG. 2) and the vial placed into the sample module 46. The sample 88 may be mixed by use of the vibratory motor 51 (FIG. 21) and incubated to the amplification temperature by use of the heating element 13. During amplification or after amplification is believed to be complete, power may be applied to the first light source 52 and luminescence of the first fluorophore in the sample may be detected by the first detector 60 (FIG. 5). Power may also be applied to the second light source 54 (preferably when power is not applied to the first light source so as to avoid detection of scattered light) and luminescence of the second fluorophore in the sample may be detected by the second detector 58. In various embodiments, the first and second light sources 52, 54 may alternately be powered during amplification to detect duplexed DNA sequences.

Generally, the detectors 60, 58 are capable of measuring the intensity of luminescence from the sample 88 (e.g., are able to measure voltage). The intensity of luminescence after application of the first light source may be correlated to the presence of a first DNA sequence in the DNA segment under analysis and the intensity of luminescence after application the second light source may be correlated to the presence of a second DNA sequence in the DNA segment. Typically, increases in luminescence indicate a proportional increase in the amplification of the DNA sequence at issue; however, it should be understood that, in certain embodiments, decreasing luminescence may indicate amplification of the DNA segment.

It should be noted that the portable instrument described herein is well-suited for detecting DNA sequences in a variety of different applications. Examples include use at the point-of-grain delivery to verify that delivered grain contains a DNA sequence (e.g., as in seed manufacturing) or does not contain a sequence (e.g., as in regulatory applications to verify that biotech crops are not being purchased for processing or export). Other applications include crop variety registrations and field testing. In this regard, the system and methods described herein may be used to detect DNA sequences in soybeans. In some particular embodiments, the system may be used to detect a first soybean gene (e.g., glyphosate resistance) and to detect a second gene present in soybeans generally (e.g., the endogenous soybean gene lectin). This second gene serves as an internal control for the reaction and the instrument, i.e., when the instrument does not detect a gene of interest, an indication that the internal control gene was amplified indicates that the sample was prepared properly and that the instrument performed properly. In this regard, it should be understood that in certain embodiments the portable system may be used without a control (i.e., a single probe is used or multiple probes are used for multiple targets without a control).

While the system and methods of the present disclosure have been generally described as capable of detecting two DNA sequences of interest, the system and methods may be used to detect more than two DNA sequences without departing from the scope of the present disclosure. For instance, the sample may contain three of more fluorophore probes and one or more of the light sources and detectors may be configured to emit or detect different wavelength bands of light. In this regard, it should be noted that while the system and methods of the present disclosure have been described with reference to analysis of plant material, the systems and methods are also suitable for animal agriculture and veterinary applications (e.g., as in animal breed verifications, disease detection) or in human health (e.g., disease detection) or in forensic applications.

Figure 23:
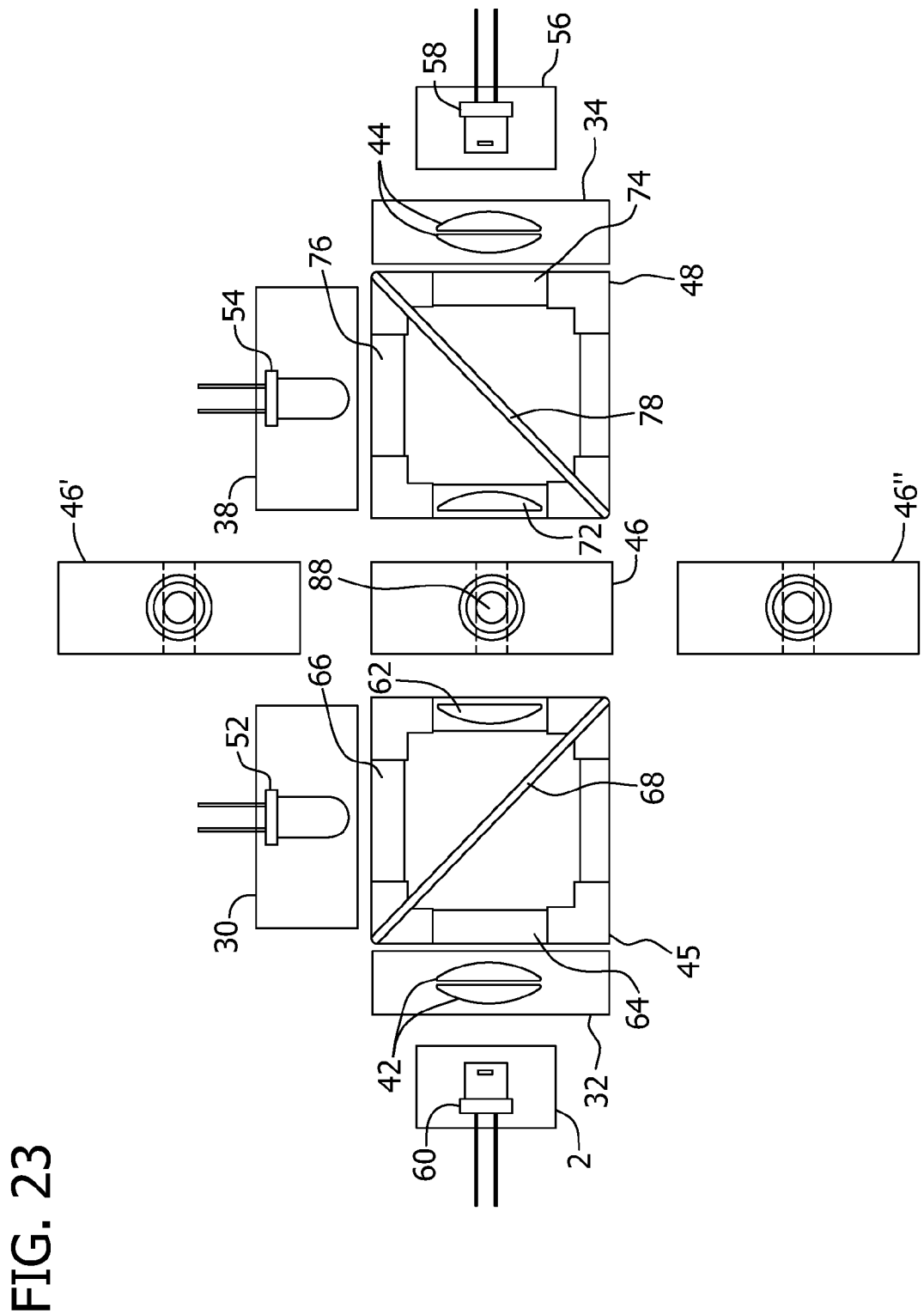
FIG. 23 is a partial schematic top view of the portable system with a liner array of sample modules shown.

As stated above, in certain embodiments, the system may also be used to analyze more than one sample. Referring now to FIG. 23, a linear array of sample modules 46, 46', 46" may be moved relative to the other parts of the system (or the other parts moved relative to the sample modules) including the first and second optics modules 45, 48, first and second lens housing 32, 34, first and second light source housings 30, 38 and first and second detector housings 2, 56. The array may contain any number of sample modules and exemplary arrays may include from about 2 to about 8

EXAMPLES

Example 1

Detection of Roundup Ready2Yield® DNA Sequence and an Internal Control Gene This example describes a testing protocol used to determine whether a sample of soybeans contains the Roundup Ready2Yield® trait. Soybean samples were collected and ground and stored at −80° C. A lysis buffer (4 ml) containing 0.2 M NaOH was added to a reagent tube. Ground soybeans (350-400 mg) were added to the reagent tube. The tube was shaken for 5 minutes with inversion and incubated at room temperature for one minute.

A rehydration buffer was prepared (46.5 ml). The buffer included distilled water, 15 mM magnesium acetate, 1.6 wt% polyethylene glycol, 107.5 mM potassium acetate and 37.6 mM tris acetate. A portion of the rehydration buffer was added to a reagent tube (46.5 µl) and stored at −20° C. Seed lysate (1 µl) was added to a reagent tube containing thawed rehydration buffer (46.5 µl). The reagent tube was votexed for several seconds to mix the sample.

RPA reagent pellets were obtained from TwistDX (Cambridge, UK). The lyophilized pellets contained two fluorophore probes, nucleotides, DNA polymerase, primers, recombinase, DNA binding proteins, ATP, phosphocreatine, creatine kinase, crowding agents, recombinase loading agents, trehalose and exonuclease. One fluorescent probe and associated primers were specific to the endogenous soybean gene lectin, which was used as an internal control with FAM used as the fluorescent dye. The second fluorescent probe and associated primers were specific to Roundup Ready2Yield® soybeans with TAMRA used as the fluorescent dye. FAM is characterized by a peak excitation near 492 mm and a peak emission at 518 mm. TAMRA is characterized by a peak excitation near 543 mm and a peak excitation near 567 mm. The reaction pellets were stored at −80° C. before use.

The contents of the rehydration buffer tube were transferred to the sample vial containing the RPA pellet. The tube was shaken and placed in the portable system shown in FIGS. 1-21. The sample module of the system was pre-incubated to 39° C. The sample was mixed by the system for 60 seconds after incubating for 3 seconds. The sample was mixed again for 30 seconds after being in the sample module for 5 minutes. The sample was analyzed after 10 minutes and data recordation was stopped 2 minutes later.

Figure 24:
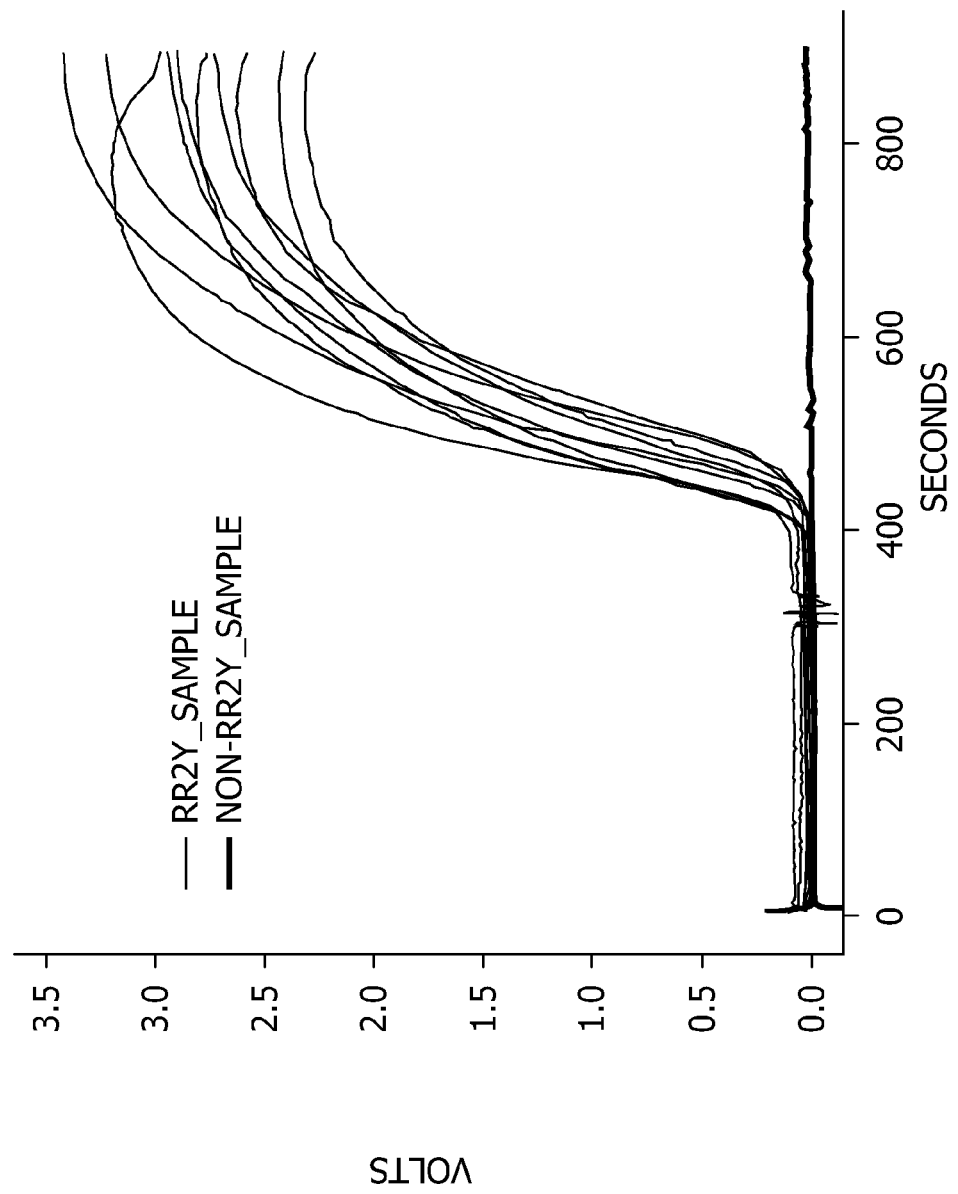
FIG. 24 is a graph of the fluorescence emitted from reaction mixtures of amplified DNA of various soybean samples containing a fluorescent dye (FAM) and primers specific to the soybean gene lectin according to Example 1.
Figure 25:
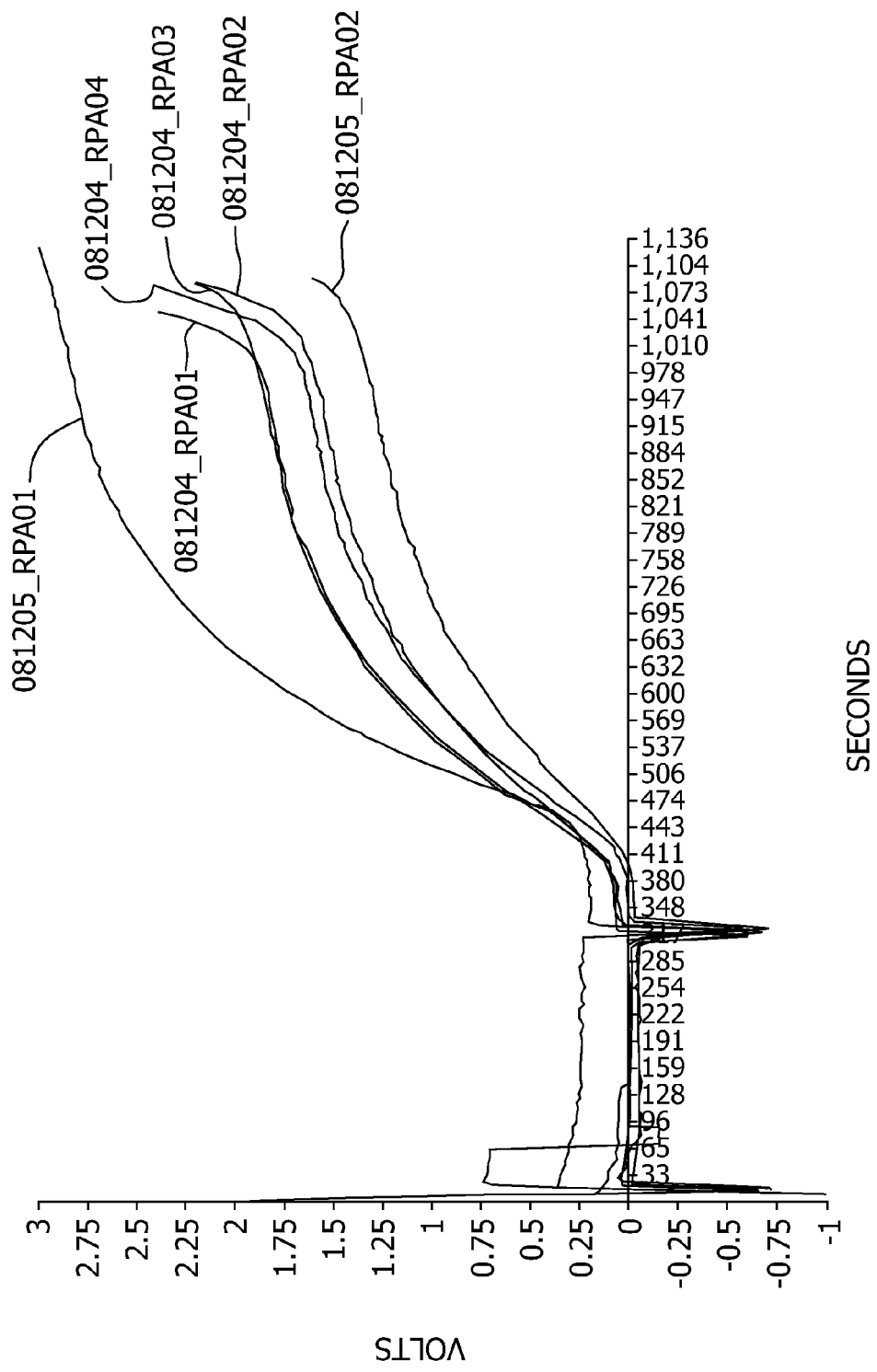
FIG. 25 is a graph of the fluorescence emitted from reaction mixtures of amplified DNA of various soybean samples containing a fluorescent dye (TAMRA) and primers specific to the Roundup Ready2Yield® soybeans.
Figure 26:
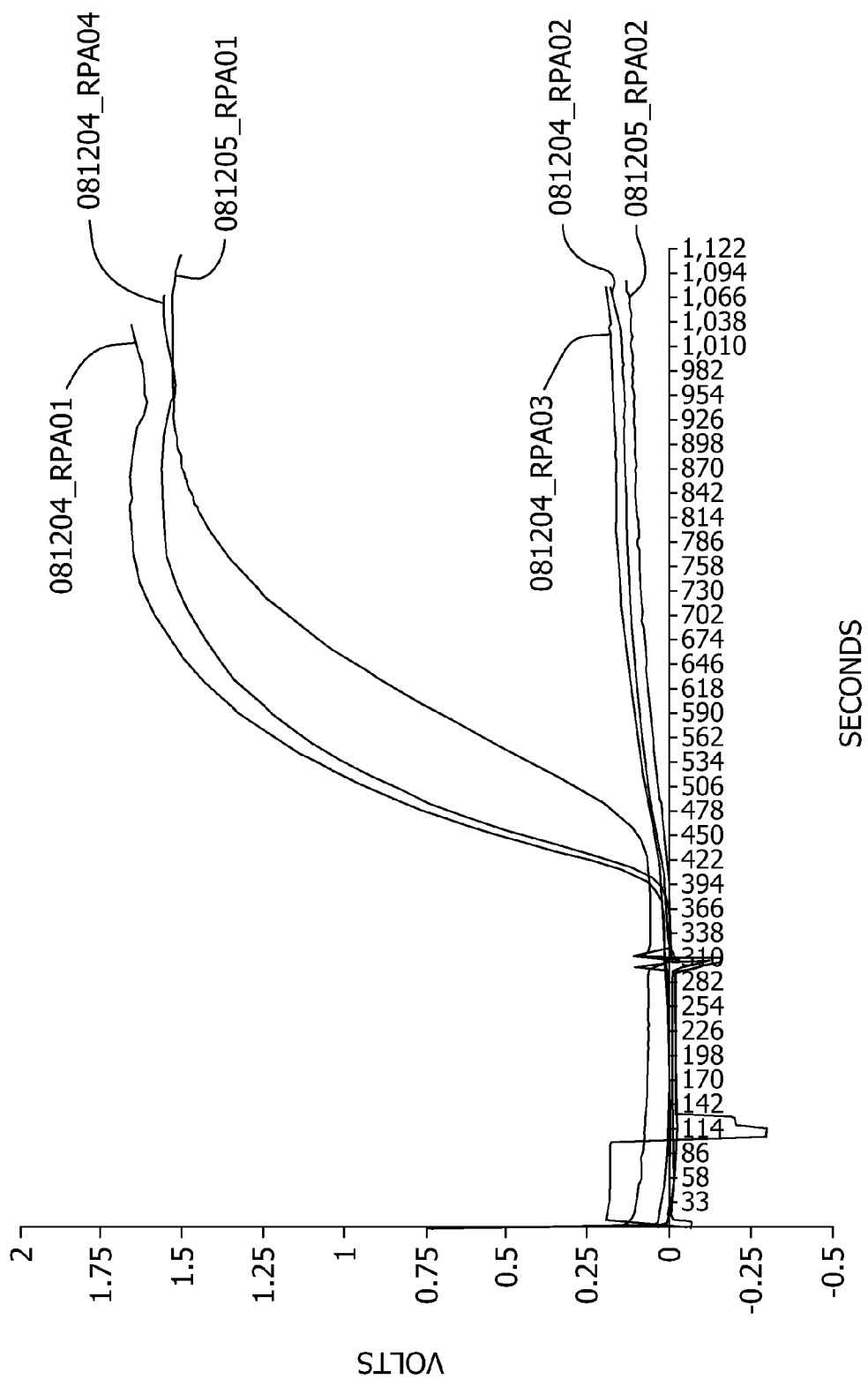
FIG. 26 is a graph of the fluorescence emitted from reaction mixtures of amplified DNA of the soybean samples of FIG. 25 containing a fluorescent dye (FAM) and primers specific to the soybean gene lectin according to Example 1.

Exemplary fluorescence plots for the TAMRA dye are shown in FIGS. 24 and 26 and an exemplary fluorescence plot for the FAM dye is shown in FIG. 25. As seen in FIG. 24, a portion of the samples tested positive for a Roundup Ready2Yield® trait ("RR2Y_Sample") and several samples tested negative for the trait ("Non-RR2Y_SAMPLE"). As can be seen from the FAM plot of FIG. 25, all soybean samples tested positive for the lectin gene. As seen in FIG. 26, a portion of the samples tested for the lectin gene in FIG. 25 did not have the Roundup Ready2Yield® trait (i.e., the samples that increased only marginally in volts) and a portion did contain the trait (i.e., the samples that began to exhibit significantly higher voltage at about 400 to 475 seconds).

This written description uses examples to disclose the invention, including the best mode, and also to enable any person skilled in the art to practice the invention, including making and using any devices or systems and performing any related methods. The patentable scope of the invention may include other examples that occur to those skilled in the art. Such other examples are intended to be within the scope of the invention.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of the present invention or the embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description and shown in the accompanying drawings shall be interpreted as illustrative and not in a limiting sense.

What is claimed is:

1. A method for determining whether a first DNA sequence and a second DNA sequence are present in a sample by use of a portable system, the method comprising:
    combining template DNA with RPA reagents in a reaction vial to form a reaction mixture;
    placing the reaction vial in a sample module of the portable system, the portable system comprising:
        a first optics module attached to a mounting plate and comprising a first optics module housing, a first excitation filter, a first dichroic mirror, a first lens and a first emission filter;
        a second optics module attached to the mounting plate and comprising a second optics module housing, a second excitation filter, a second dichroic mirror, a second lens and a second emission filter;
        the sample module being attached to the mounting plate and comprising a sample module housing, a heating element, a vibratory motor, a solid coupling for receiving the sample vial, the solid coupling being attached to the vibratory motor, a vibratory insulating spacer attached to the vibratory motor to prevent vibrations from traveling to the mounting plate during operation of the vibratory motor, wherein the first optics module housing and the second optics module housing are separated from the sample module housing;
    applying power to the vibratory motor to cause the solid coupling to vibrate, wherein vibration of the solid coupling translates to the reaction mixture to cause mixing of the reaction mixture;
    incubating the reaction mixture by use of the heating element to an amplification temperature at which DNA is amplified by an RPA process to form an amplified sample mixture;

applying power to a first light source to cause light to travel through the first optics module and to the amplified sample mixture to cause the sample mixture to fluoresce;

applying power to a second light source to cause light to travel through the second optics module and to the amplified sample mixture to cause the sample mixture to fluoresce;

correlating the intensity of fluorescence of the amplified sample mixture after application of the first light source to the presence of a first DNA sequence in the template DNA; and correlating the intensity of fluorescence of the amplified sample mixture after application of the second light source to the presence of a second DNA sequence in the template DNA.

2. A method as set forth in claim 1 wherein the DNA segment is from a sample of soybeans.

3. A method as set forth in claim 1 wherein at least one of the first DNA sequence or the second DNA sequence represents a gene conferring glyphosate resistance.

4. A method as set forth in claim 1 wherein the portable system further comprises a third lens and a fourth lens.

5. A method as set forth in claim 4 wherein light emitted from the first light source travels through the first excitation filter, is reflected by the first dichroic mirror and travels through the first lens to the amplified sample mixture; light emitted from the amplified sample mixture in response to light absorbed from the first light source travels through the first lens, through the first dichroic mirror and through the first emission filter to a first emission detector; light emitted from the second light source travels through the second excitation filter, is reflected by the second dichroic mirror and travels through the second lens to the amplified sample mixture; light emitted from the amplified sample mixture in response to light absorbed from the second light source travels through the second lens, through the second dichroic mirror and through the second emission filter to a second emission detector.

6. A method as set forth in claim 5 wherein the first light source and second light source emit light of two different wavelengths.

7. A method as set forth in claim 5 wherein the reaction mixture comprises a first fluorophore and a second fluorophore and the first detector detects light emitted from the first fluorophore and the second detector detects light emitted from the second fluorophore.

8. A method as set forth in claim 1 wherein the first excitation filter, first lens and first emission filter are attached to the first optics module housing and the second excitation filter, second lens and second emission filter are attached to the second optics module housing.

9. A method as set forth in claim 1 wherein the first optics module housing and the sample module housing are separated by a first space and the second optics module housing and the sample module housing are separated by a second space.

10. A method as set forth in claim 1 wherein the portable system comprises no more than one sample module and wherein the sample module is capable of receiving no more than one sample vial.

11. A method as set forth in claim 4 wherein the first, second, third and fourth lenses; first and second emission filters;

and first and second dichroic mirrors are generally intersected by a first plane.

12. A method as set forth in claim 11 wherein the first light source, first excitation filter and first dichroic mirror are generally intersected by a second plane and the second light source, second emission filter and second dichroic mirror are generally intersected by a third plane.

13. A method as set forth in claim 12 wherein the second plane and the third plane are generally perpendicular to the first plane.

* * * * *